US008435789B2

(12) United States Patent
Burr et al.

(10) Patent No.: US 8,435,789 B2
(45) Date of Patent: *May 7, 2013

(54) MEDIA, KITS, SYSTEMS AND METHODS FOR THE MICROPROPAGATION OF BAMBOO

(75) Inventors: Randall W. Burr, Mount Vernon, WA (US); Jackie Heinricher, Anacortes, WA (US)

(73) Assignee: Provitro Biosciences LLC, Mount Vernon, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/468,690

(22) Filed: May 10, 2012

(65) Prior Publication Data

US 2012/0220036 A1    Aug. 30, 2012

Related U.S. Application Data

(63) Continuation of application No. 13/258,653, filed as application No. PCT/US2011/024936 on Feb. 15, 2011.

(60) Provisional application No. 61/304,681, filed on Feb. 15, 2010.

(51) Int. Cl.
*A01H 4/00* (2006.01)

(52) U.S. Cl.
USPC ......... 435/420; 435/431; 435/430.1; 800/320

(58) Field of Classification Search .................. None
See application file for complete search history.

(56) References Cited

U.S. PATENT DOCUMENTS

| 5,334,530 | A | 8/1994 | Woods et al. |
| 5,750,401 | A | 5/1998 | Phadke et al. |
| 6,677,154 | B2 * | 1/2004 | Gielis et al. .................. 435/420 |
| 7,052,912 | B1 | 5/2006 | Woods et al. |
| 2002/0086425 | A1 | 7/2002 | Gielis et al. |
| 2003/0110531 | A1 | 6/2003 | Dan et al. |
| 2004/0143868 | A1 | 7/2004 | Ainley et al. |
| 2004/0221506 | A1 | 11/2004 | Tisserat |
| 2008/0261310 | A1 | 10/2008 | Okole et al. |
| 2009/0205066 | A1 | 8/2009 | Browse et al. |

FOREIGN PATENT DOCUMENTS

| WO | WO 02/14520 A2 | 2/2002 |
| WO | WO 2004108903 A2 | 12/2004 |
| WO | WO 2010129737 A2 | 11/2010 |
| WO | WO 2011019984 A2 | 2/2011 |

OTHER PUBLICATIONS

Werbrouck et al. (Physiologia Plantarum 98: 291-297. 1996.).*
Bhatti et al., "Current trends and future prospects of biotechnological interventions through tissue culture in apple", *Plant Cell Rep.*, 2010, 29:1215-1225.
International Search Report based on International Patent Application No. PCT/US12/25018, mailed on Jun. 20, 2012.
Written Opinion of International Searching Authority based on International Patent Application No. PCT/US12/25018, mailed on Jun. 20, 2012.
Agnihotri et al., "Improved in vitro shoot multiplication and rooting of *Dendrocalamus hamiltonii* Nees et Arn. Ex Munro: production of genetically uniform plants and field evaluation", *Acta Physiol Plant* (2003) 31:961-967.
Aremu et al., "Topolins: A panacea to plant tissue culture challenges?" *Plant Cell Tiss. Organ Cult.* (Jul. 24, 2011), DOI 10.1007/s11240-011-0007-7.
Bairu et al., "Optimizing the micropropagation protocol for the endangered *Aloe polyphylla*: can meta-topolin and its derivatives serve as replacement for benzyladenine and zeatin?", *Plant Cell Tiss. Organ Cult.* (2007) 90:15-23.
Baldwin et al., "Propagation Methods for Rivercane [*Arundinaria gigntea* L. (Walter) Muhl.]", *CASTANEA* (2009), 74(3):300-316.
Banik et al., "In Vitro Regeneration of Multiple Shoots in Three Bamboo Species", Plant Tissue Cult. (1993) 3(2): 101-106.
Baroja-Fernandez et al. "Aromatic cytokinins in micropropagated potato plants", *Plant Physiol. Biochem.* (2002) 40:217-224.
Bogaert et al., "New Aromatic Cytokinins can Make the Difference", *Acta Hort.* (2006), 725:265-270.
De Diego et al., "In Vitro Regeneration of *Pinus* spp. Adult Trees: New Method for Obtaining Clonal Plants" *Acta Hort.* (2010), 865:361-366.
Dobranszki et al., "Effect of conditioning apple shoots with meta-topolin on the morphogenic activity of in vitro leaves", *Acta Agronomica Hungarica*, (2002), 50(2): 117-126.
Dobranszki et al., "How Can Different Cytokinins Influence the Process of Shoot Regeneration from Apple Leaves in 'Royal Gala' and M.26", *Acta Hort.* (2006), 725:191-196.
Escalona et al., "The effect of meta-topolin on plantain propagation using a temporary immersion bioreactor", *InfoMusa*, (2009) 12(2):28-30.
Khan et al., "Thidiazuron induced somatic embryogenesis and plant regeneration in *Capsicum anmuum*", *Biologica Plantarum* (2006) 0 (4): 789-792.
Lin et al. "Effect of thidiazuron on vegetative tissue-derived somatic embryogenesis and flowering of bamboo *Bambusa edulis*" *Plant Cell, Tissue and Organ Culture* (2004), 76:75-82.
Lin et al. "Stamen-less inflorescence proliferation of *Bambusa edulis*" *Scientia Horticulturae* (2005) 107:76-80.
Magyar-Tabori et al., "Effect of cytokinin content of the regeneration media on in vitro rooting ability of adventitious apple shoots", *Scientia Horticulturae*, (2011) doi:10.1016/j.scienta.2011.05.011.
Mata-Rosas et al., "In vitro regeneration of *Lycaste aromatica* (Graham ex Hook) Lindl. (Orchidaceae) from pseudobulb sections" *Plant Biotechnol Rep.* (2010) 4:157-163.

(Continued)

*Primary Examiner* — David T Fox
*Assistant Examiner* — Jared Shapiro
(74) *Attorney, Agent, or Firm* — Cooley LLP

(57) ABSTRACT

Disclosed herein are media, kits, systems and methods for achieving micropropagation of bamboo on a commercially-relevant scale.

18 Claims, No Drawings

OTHER PUBLICATIONS

Meiners et al., "Efficient in vitro regeneration systems for *Vaccinium* species" *Plant Cell Tiss. Organ Cult.* (2007) 89:169-176.

Mishra et al., "A micropropagation system for cloning of *Bambusa tulda* Roxb.", *Scientia Horticulturae* (2008), 115:315-318.

Nas et al., "The effects of explant and cytokinin type on regeneration of *Prunus microcarpa*", *Scientia Horticulturae* (2010) 126:88-94.

Ramanayake et al., "Root induction in three species of bamboo with different rooting abilities", *Scientia Horticulturae* (2008) 118:270-273.

Ramanayake et al., "In vitro shoot proliferation and enhancement of rooting for the large-scale propagation of yellow bamboo (*Bambusa vulgaris* 'Striata')", *Scientia Horticulturae* (2006) 110:109-113.

Roels et al., "Optimization of plantain (Musa AAB) micropropagation by temporary immersion system", *Plant Cell, Tiss. and Organ Cult.* (2005) 82: 57-66.

Rosales et al., "Effect of cytokinins of the in vitro propagation of Mexican Agaves", *Articulo Cientifico Rev. Fitotec. Mex* (2005) 31(4): 317-322, Abstract only.

Sanjaya et al. "Micropropagation of *Pseudoxytenanthera stocksii* Munro", *In vitro Cell. Biol.-Plant* (2005) 41:333-337.

Saxena et al., In vitro propagation of the bamboo (*Bambusa tulda* Roxb.) through shoot proliferation (1990): Plant Cell Reports (1990) 9:431-434.

Saxena et al., "In vitro clonal multiplication of 4-year-old plants of the bamboo, *dendrocalamus longispathus* Kurz", *In vitro Cell. Biol.-Plant* (1993), 29P:135-142.

Vasudevan et al., "Cytokinin and explant types influence in vitro plant regeneration of Leopard Orchid (*Ansellia africana* Lindl.)" *Plant Cell Tiss. Organ Cult.* (2011) DOI 10.1007/s11240-011-9964-0.

Vinayak et al., "Efficacy of non-purine and purine cytokinins on shoot regeneration iv vitro in sugarcane", *Indian Journal of Biotechnology*, (2009), 8:227-231.

Werbrouck et al., "Meta-topolin, an alternative to benzyladenine in tissue culture?" *Physiologia Plantarum*, (1996) 98:291-297.

Zhang et al., "Improving 'Bing' sweet cherry fruit quality with plant growth regulators". *Scientia Horticulturae*, doi:10.1016/j.scienta.2010.11.006.

Zhang et al., "Somatic embryogenesis and organogenesis in *Dendrocalamus hamiltonii*", *Plant Cell Tiss. Organ Cult.* (2010) DOI 10.1007/s11240-010-9783-8.

Murashige and Skoog medium. [Retrieved from the Internet Jun. 14, 2011: http://en.wikipedia.org/w/index.php?title=Murashige_and_Skoog_dedium&oldid=343630481] (Feb. 12, 2010).

International Search Report based on International Patent Application No. PCT/US11/24936, mailed on Jun. 22, 2011.

Bock, "Cracking the code to 'The perfect plant' opens a path to saving the planet", The New York Times, Sunday Magazine, published on Apr. 20, 2008.

Online Press Release, "Booshoot Founder & CEO Jackie Heinricher Honored as Visionary Entrepreneur by Martha Stewart", published on Oct. 9, 2009; retrieved from online on Jan. 18, 2013.

Raver, "A Cane the World Can Lean on", The New York Times, published on Jul. 5, 2007, retrieved from online on Jan. 18, 2013.

Heffernan, "Healing the Planet with Earth-Friendly Bamboo Products", Reader's Digest, published on Dec. 2008; retrieved from online on Jan. 18, 2013.

Gandel, "Bamboo Steps Up", Smithsonian Magazine, Mar. 21, 2008, published on Mar. 21, 2008; retrieved from online on Jan. 18, 2013.

Bock, "Propagating the Big Idea", Pacific Northwest, The Seattle Times Sunday Magazine, published on Apr. 20, 2008.

* cited by examiner

MEDIA, KITS, SYSTEMS AND METHODS FOR THE MICROPROPAGATION OF BAMBOO

CROSS-REFERENCE TO RELATED APPLICATION

This application claims priority to and is a continuation of U.S. patent application Ser. No. 13/258,653, filed Sep. 22, 2011, pending, which is a National Stage Entry of International Patent Application No. PCT/US2011/024936, filed Feb. 15, 2011, which claims priority to U.S. Provisional Patent Application No. 61/304,681, filed Feb. 15, 2010. The entire disclosures of U.S. patent application Ser. No. 13/258, 653, International Patent Application No. PCT/US2011/024936 and U.S. Provisional Patent Application No. 61/304,681 are incorporated by reference herein.

FIELD OF THE DISCLOSURE

Disclosed herein are media, kits, systems and methods for the micropropagation of bamboo.

BACKGROUND OF THE DISCLOSURE

The subfamily Bambusoideae (of the family Poaceae), comprises both woody and herbaceous bamboos. At present roughly 120 genera of temperate and tropical woody bamboos are recognized. Bamboos are versatile plants with many different applications. It has been estimated that approximately 2.2 billion people worldwide use bamboo to some extent, and in 1985 the global revenue attributable to bamboo was estimated around U.S. $4.5 billion. The market for bamboo is also expanding. Bamboo shoots are a staple of Asian cuisine, and bamboo is found in a number of products including toothpicks, brooms, poles for viticulture and arboriculture, landscaping materials, parquet flooring, laminate materials, furniture, handicrafts and other household items. In addition, bamboo is becoming an important source of textile material as a component of paper production and as a source of structural timber.

Bamboo is considered an environmentally friendly "green" product. One of the characteristics that gives bamboo its green reputation is its extremely rapid growth rate. Bamboo is the fastest growing woody plant in the world, achieving growth rates of well over three feet per day. It achieves this rate of growth in part because of its rhizome system, which is capable of providing a great deal of energy toward shoot growth.

Despite bamboo's rapid growth rate, it has other characteristics that make it a difficult crop to manage. Perhaps the greatest difficulty comes from the fact that many commercially important bamboos only flower at intervals of as long as 60-130 years. Compounding the difficulties of this long flowering cycle is the fact that many bamboos exhibit mass (or gregarious) flowering, with all plants in the population flowering simultaneously. For example, *Phyllostachys bambusoides* flowers at an interval of 130 years, and in this species all plants of the same stock flower at the same time, regardless of differences in geographic locations or climatic conditions. After flowering, the bamboo dies.

Bamboo's lengthy flowering interval and propensity for mass flowering makes it very difficult to obtain seeds for propagation. Compounding this problem is the fact that bamboo seeds, even when they are available, remain viable for no more than 3-6 months.

As a result of these difficulties with the propagation of bamboo by seed, bamboo typically is propagated by asexual techniques such as clump division and cutting. These asexual propagation techniques, however, are insufficient to meet projected world demand because both their capacity to produce mass scale production, and their practical efficiency, are too low. In addition many asexual propagation methods have the downside of failing to eliminate pathogens present in the parent plants.

A method to achieve large scale production of bamboo is highly desirable. Micropropagation (also known as tissue culturing with the terms used interchangeably herein), is an excellent method to achieve this aim.

Micropropagation is not unlike growing plants from cuttings. However, unlike plants grown from cuttings, micropropagated plants are grown in vitro in sterile media. Typically, the media comprises agar, with the addition of various compounds such as nutrients, inorganic salts, growth regulators, sugars, vitamins and other compounds.

A benefit to tissue culturing plants is that the plants can be grown in a sterile environment so that they remain disease free. Other benefits include the ability to grow very large numbers of plants in a small space, the reduced water and nutrient needs of micropropagated plants, and the rapid multiplication of tissues that can in turn be used to yield more tissue culture material. Moreover micropropagation is very flexible and rapid upscaling is possible (within 1 year nearly one million plants can be produced from any genotype). Such short time frames and large numbers cannot be rivaled by any conventional method. Tissue culturing also provides for the production of high quality plants which are easy to transport and deliver.

Some papers have been published which address tissue culturing of bamboo. In practice, however (i.e., for large or mass scale propagation of bamboos), the methods described in these papers do not translate into commercially viable propagation systems.

The difficulties encountered in tissue culturing bamboo are high incidences of endogenous or surface contaminations and browning, factors related to dormancy or topophysis and hyperhydricity. The present disclosure provides media, systems and methods that overcome these difficulties allowing the commercial-scale asexual production of bamboo.

SUMMARY OF THE DISCLOSURE

The present disclosure overcomes the difficulties encountered in the commercial-scale asexual production of bamboo by providing effective media, systems and methods for tissue culturing bamboo.

One embodiment disclosed herein is a media for micropropagating bamboo wherein said media comprises meta-topolin or thidiazuron. In another embodiment, the media comprises meta-topolin and thidiazuron. In another embodiment, the media is b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

Embodiments disclosed herein also include systems for the micropropagation of bamboo. In one embodiment, the system comprises a kit comprising a media comprising meta-topolin or thidiazuron. In another embodiment, meta-topolin and thidiazuron are found in the same media or in separate media. In another embodiment, the media is b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

Embodiments disclosed herein also include methods of micropropagating bamboo. In one embodiment, the method comprises culturing bamboo explants, cultures and/or shoots in media comprising meta-topolin and/or thidiazuron. In another embodiment, the meta-topolin and thidiazuron are found in the same media or in separate media. In another embodiment, the media is b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

Embodiments include, without limitation:

1. A media comprising, consisting essentially of or consisting of:

| Component | mg/L (unless otherwise noted) | Component | mg/L (unless otherwise noted) |
|---|---|---|---|
| $NH_4NO_3$ | 1650 ± 2 | $KH_2PO_4$ | 170 ± 2 |
| $KNO_3$ | 1900 ± 2 | $FeSO_4$ | 55.7 ± 0.2 |
| $Ca(NO_3)_2$ | 550 ± 2 | $Na_2EDTA$ | 74.6 ± 0.2 |
| $MgSO_4$ | 370 ± 2 | $Na_2H_2PO_4$ | 170 ± 2 |
| $MnSO_4$ | 16.9 ± 0.2 | myo-Inositol | 100 ± 2 |
| $ZnSO_4$ | 8.6 ± 0.2 | Thiamine | 0.4 ± 0.2 |
| $CuSO_4$ | 0.025 ± .002 | NAA | 0.05 ± .02 |
| $CaCl_2$ | 440 ± 2 | BAP | 1 ± 0.2 |
| KI | 0.83 ± .02 | Meta-topolin | 5 ± 2 |
| $CoCl_2$ | 0.025 ± .002 | Sugar g/L | 30 ± 2 |
| $H_3BO_3$ | 6.2 ± .02 | Agar g/L | 5.5 ± 0.2 |
| $Na_2MoO_4$ | 0.25 ± .02 | | | or

| Component | mg/L (unless otherwise noted) | Component | mg/L (unless otherwise noted) |
|---|---|---|---|
| $NH_4NO_3$ | 1650 ± 2 | $KH_2PO_4$ | 170 ± 2 |
| $KNO_3$ | 1900 ± 2 | $FeSO_4$ | 55.7 ± 0.2 |
| $Ca(NO_3)_2$ | 550 ± 2 | $Na_2EDTA$ | 74.6 ± 0.2 |
| $MgSO_4$ | 370 ± 2 | $Na_2H_2PO_4$ | 170 ± 2 |
| $MnSO_4$ | 16.9 ± 2 | myo-Inositol | 100 ± 2 |
| $ZnSO_4$ | 8.6 ± 0.2 | Thiamine | 0.4 ± 0.2 |
| $CuSO_4$ | 0.025 ± .002 | NAA | 0.05 ± .02 |
| $CaCl_2$ | 440 ± 2 | BAP | 1 ± 0.2 |
| KI | 0.83 ± .02 | Thidiazuron | 0.75 ± .02 |
| $CoCl_2$ | 0.025 ± .002 | Meta-topolin | 5 ± 2 |
| $H_3BO_3$ | 6.2 ± 0.2 | Sugar g/L | 30 ± 2 |
| $Na_2MoO_4$ | 0.25 ± .02 | Agar g/L | 5.5 ± 0.2 |

2. A method of micropropagating bamboo comprising exposing a bamboo explant to a media of embodiment 1.

3. A method according to embodiment 2 further comprising exposing a bamboo shoot to a b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

4. A method according to embodiment 3 further comprising exposing a bamboo shoot to a media that supports transition to ex vitro conditions.

5. A method according to embodiment 3 wherein said method produces 100,000 bamboo shoots from an explant.

6. A method according to any of embodiments 2, 3, 4 or 5 wherein said method further comprises obtaining an explant.

7. A method according to embodiment 6 wherein said explant is the third node from the base of a bamboo cane.

8. A kit comprising a media consisting of:

| Component | mg/L (unless otherwise noted) | Component | mg/L (unless otherwise noted) |
|---|---|---|---|
| $NH_4NO_3$ | 1650 ± 2 | $KH_2PO_4$ | 170 ± 2 |
| $KNO_3$ | 1900 ± 2 | $FeSO_4$ | 55.7 ± 0.2 |
| $Ca(NO_3)_2$ | 550 ± 2 | $Na_2EDTA$ | 74.6 ± 0.2 |
| $MgSO_4$ | 370 ± 2 | $Na_2H_2PO_4$ | 170 ± 2 |
| $MnSO_4$ | 16.9 ± 0.2 | myo-Inositol | 100 ± 2 |
| $ZnSO_4$ | 8.6 ± 0.2 | Thiamine | 0.4 ± 0.2 |

-continued

| Component | mg/L (unless otherwise noted) | Component | mg/L (unless otherwise noted) |
|---|---|---|---|
| CuSO$_4$ | 0.025 ± .002 | NAA | 0.05 ± .02 |
| CaCl$_2$ | 440 ± 2 | BAP | 1 ± 0.2 |
| KI | 0.83 ± .02 | Meta-topolin | 5 ± 2 |
| CoCl$_2$ | 0.025 ± .002 | Sugar g/L | 30 ± 2 |
| H$_3$BO$_3$ | 6.2 ± .02 | Agar g/L | 5.5 ± 2 |
| Na$_2$MoO$_4$ | 0.25 ± .02 | | | or

| Component | mg/L (unless otherwise noted) | Component | mg/L (unless otherwise noted) |
|---|---|---|---|
| NH$_4$NO$_3$ | 1650 ± 2 | KH$_2$PO$_4$ | 170 ± 2 |
| KNO$_3$ | 1900 ± 2 | FeSO$_4$ | 55.7 ± 0.2 |
| Ca(NO$_3$)$_2$ | 550 ± 2 | Na$_2$EDTA | 74.6 ± 0.2 |
| MgSO$_4$ | 370 ± 2 | Na$_2$H$_2$PO$_4$ | 170 ± 2 |
| MnSO$_4$ | 16.9 ± 2 | myo-Inositol | 100 ± 2 |
| ZnSO$_4$ | 8.6 ± 0.2 | Thiamine | 0.4 ± 0.2 |
| CuSO$_4$ | 0.025 ± .002 | NAA | 0.05 ± .02 |
| CaCl$_2$ | 440 ± 2 | BAP | 1 ± 0.2 |
| KI | 0.83 ± .02 | Thidiazuron | 0.75 ± .02 |
| CoCl$_2$ | 0.025 ± .002 | Meta-topolin | 5 ± 2 |
| H$_3$BO$_3$ | 6.2 ± 0.2 | Sugar g/L | 30 ± 2 |
| Na$_2$MoO$_4$ | 0.25 ± .02 | Agar g/L | 5.5 ± 0.2 |

9. A kit according to embodiment 8 further comprising a b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

10. A kit according to embodiment 8 or 9 further comprising a media that supports transition to ex vitro conditions.

11. A kit according to embodiment 8, 9, or 10 further comprising an explant.

12. A method of micropropagating bamboo comprising exposing a bamboo explant to a media comprising meta-topolin and/or thidiazuron.

13. A method according to embodiment 12 wherein said media comprises b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

14. A method according to embodiment 12 wherein the explant is the third node from the base of a bamboo cane.

15. A media comprising a b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

16. A media consisting essentially of a b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media; b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

17. A media consisting of a b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

18. A kit comprising a media according to embodiment 15, 16 or 17.

19. A method of micropropagating bamboo utilizing a media according to embodiment 1, 15, 16 or 17.

20. A method of micropropagating bamboo utilizing a kit according to embodiment 8, 9, 10, 11 or 18.

Additional embodiments include:

21. A media comprising, consisting essentially of or consisting of:

| Component | mg/L (unless otherwise noted) | Component | mg/L (unless otherwite noted) |
|---|---|---|---|
| NH$_4$NO$_3$ | 1650 ± 2 | KH$_2$PO$_4$ | 170 ± 2 |
| KNO$_3$ | 1900 ± 2 | FeSO$_4$ | 55.7 ± 0.2 |
| Ca(NO$_3$)$_2$ | 550 ± 2 | Na$_2$EDTA | 74.6 ± 0.2 |
| MgSO$_4$ | 370 ± 2 | Na$_2$H$_2$PO$_4$ | 170 ± 2 |
| MnSO$_4$ | 16.9 ± 0.2 | myo-Inositol | 100 ± 2 |
| ZnSO$_4$ | 8.6 ± 0.2 | Thiamine | 0.4 ± 0.2 |
| CuSO$_4$ | 0.025 ± .002 | NAA | 0.05 ± .02 |
| CaCl$_2$ | 440 ± 2 | BAP | 1 ± 0.2 |
| KI | 0.83 ± .02 | Cytokinin A | 5 ± 2 |
| CoCl$_2$ | 0.025 ± .002 | Sugar g/L | 30 ± 2 |
| H$_3$BO$_3$ | 6.2 ± .02 | Agar g/L | 5.5 ± 0.2 |
| Na$_2$MoO$_4$ | 0.25 ± .02 | | | or

| Component | mg/L (unless otherwise noted) | Component | mg/L (unless otherwise noted) |
|---|---|---|---|
| NH$_4$NO$_3$ | 1650 ± 2 | KH$_2$PO$_4$ | 170 ± 2 |
| KNO$_3$ | 1900 ± 2 | FeSO$_4$ | 55.7 ± 0.2 |
| Ca(NO$_3$)$_2$ | 550 ± 2 | Na$_2$EDTA | 74.6 ± 0.2 |
| MgSO$_4$ | 370 ± 2 | Na$_2$H$_2$PO$_4$ | 170 ± 2 |
| MnSO$_4$ | 16.9 ± 2 | myo-Inositol | 100 ± 2 |
| ZnSO$_4$ | 8.6 ± 0.2 | Thiamine | 0.4 ± 0.2 |
| CuSO$_4$ | 0.025 ± .002 | NAA | 0.05 ± .02 |
| CaCl$_2$ | 440 ± 2 | BAP | 1 ± 0.2 |
| KI | 0.83 ± .02 | Cytokinin B | 0.75 ± .02 |
| CoCl$_2$ | 0.025 ± .002 | Cytokinin A | 5 ± 2 |
| H$_3$BO$_3$ | 6.2 ± 0.2 | Sugar g/L | 30 ± 2 |
| Na$_2$MoO$_4$ | 0.25 ± .02 | Agar g/L | 5.5 ± 0.2 | wherein cytokinin A is meta-topolin or a meta-topolin analogue as described herein and cytokinin B is thidiazuron or a thidiazuron analogue as described herein.

22. A method of micropropagating bamboo comprising exposing a bamboo explant to a media of embodiment 21.

23. A method according to embodiment 22 further comprising exposing a bamboo shoot to a b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

24. A method according to embodiment 23 further comprising exposing a bamboo shoot to a media that supports transition to ex vitro conditions.

25. A method according to embodiment 23 wherein said method produces 100,000 bamboo shoots from an explant.

26. A method according to any of embodiments 22, 23, 24 or 25 wherein said method further comprises obtaining an explant.

27. A method according to embodiment 26 wherein said explant is the third node from the base of a bamboo cane.

28. A kit comprising a media comprising, consisting essentially of or consisting of:

| Component | mg/L (unless otherwise noted) | Component | mg/L (unless otherwise noted) |
|---|---|---|---|
| NH$_4$NO$_3$ | 1650 ± 2 | KH$_2$PO$_4$ | 170 ± 2 |
| KNO$_3$ | 1900 ± 2 | FeSO$_4$ | 55.7 ± 0.2 |
| Ca(NO$_3$)$_2$ | 550 ± 2 | Na$_2$EDTA | 74.6 ± 0.2 |
| MgSO$_4$ | 370 ± 2 | Na$_2$H$_2$PO$_4$ | 170 ± 2 |
| MnSO$_4$ | 16.9 ± 0.2 | myo-Inositol | 100 ± 2 |
| ZnSO$_4$ | 8.6 ± 0.2 | Thiamine | 0.4 ± 0.2 |
| CuSO$_4$ | 0.025 ± .002 | NAA | 0.05 ± .02 |
| CaCl$_2$ | 440 ± 2 | BAP | 1 ± 0.2 |
| KI | 0.83 ± .02 | Cytokinin A | 5 ± 2 |
| CoCl$_2$ | 0.025 ± .002 | Sugar g/L | 30 ± 2 |
| H$_3$BO$_3$ | 6.2 ± .02 | Agar g/L | 5.5 ± 2 |
| Na$_2$MoO$_4$ | 0.25 ± .02 | | | or

| Component | mg/L (unless otherwise noted) | Component | mg/L (unless otherwise noted) |
|---|---|---|---|
| NH$_4$NO$_3$ | 1650 ± 2 | KH$_2$PO$_4$ | 170 ± 2 |
| KNO$_3$ | 1900 ± 2 | FeSO$_4$ | 55.7 ± 0.2 |
| Ca(NO$_3$)$_2$ | 550 ± 2 | Na$_2$EDTA | 74.6 ± 0.2 |
| MgSO$_4$ | 370 ± 2 | Na$_2$H$_2$PO$_4$ | 170 ± 2 |
| MnSO$_4$ | 16.9 ± 2 | myo-Inositol | 100 ± 2 |
| ZnSO$_4$ | 8.6 ± 0.2 | Thiamine | 0.4 ± 0.2 |
| CuSO$_4$ | 0.025 ± .002 | NAA | 0.05 ± .02 |
| CaCl$_2$ | 440 ± 2 | BAP | 1 ± 0.2 |
| KI | 0.83 ± .02 | Cytokinin B | 0.75 ± .02 |
| CoCl$_2$ | 0.025 ± .002 | Cytokinin A | 5 ± 2 |
| H$_3$BO$_3$ | 6.2 ± 0.2 | Sugar g/L | 30 ± 2 |
| Na$_2$MoO$_4$ | 0.25 ± .02 | Agar g/L | 5.5 ± 0.2 | wherein cytokinin A is meta-topolin or a meta-topolin analogue as described herein and cytokinin B is thidiazuron or a thidiazuron analogue as described herein.

29. A kit according to embodiment 28 further comprising a b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

30. A kit according to embodiment 28 or 29 further comprising a media that supports transition to ex vitro conditions.

31. A kit according to embodiment 28, 29, or 30 further comprising an explant.

32. A method of micropropagating bamboo comprising exposing a bamboo explant to a media comprising meta-topolin or a meta-topolin analogue as described herein and/or thidiazuron or a thidiazuron analogue as described herein.

33. A method according to embodiment 32 wherein said media comprises a b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

34. A method according to embodiment 32 wherein the explant is the third node from the base of a bamboo cane.

35. A media comprising a b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

36. A media consisting essentially of a b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

37. A media consisting of a b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

38. A kit comprising a media according to embodiment 35, 36 or 37.

39. A method of micropropagating bamboo utilizing a media according to embodiment 21, 35, 36 or 37.

40. A method of micropropagating bamboo utilizing a kit according to embodiment 28, 29, 30, 31 or 38.

41. A media for micropropagating bamboo wherein said media supports 10-120 day multiplication cycles at least 1 month, for at least 3 months, for at least 6 months, for at least 9 months, for at least 12 months, for at least 15 months, for at least 18 months, for at least 21 months, for at least 24 months or for at least 36 months.

42. A media according to embodiment 41 wherein said media comprises, consists essentially of or consists of b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

Additional embodiments include:

43. A media for micropropagating bamboo wherein said media comprises meta-topolin or an analogue thereof and supports 10-120 day multiplication cycles for at least six months.

44. A media according to embodiment 43 wherein said media supports 10-120 day multiplication cycles for at least one year.

45. A media according to embodiment 43 or 44 wherein said meta-topolin or analogue thereof is present in an amount from 0.0125 mg/mL-10 mg/mL.

46. A media according to embodiment 43, 44, or 45 wherein said media further comprises thidiazuron or an analogue thereof.

47. A media according to embodiment 43, 44, 45, or 46 wherein said media further comprises NAA, BAP, 2ip and/or IBA.

48. A method of micropropagating bamboo comprising culturing bamboo explants and/or shoots in a media of embodiment 43, 44, 45, 46 or 47.

49. A method of micropropagating bamboo according to embodiment 48 wherein said bamboo is *Phyllostachys bissetti; Fargesia denudata; Pleioblastus fortunei; Sasa Veitchii; Pleioblastus viridistriatus; Thamnocalamus crassinodus; Chusquea Culeo* "Cana Prieta"; Bambusa Old Hamii; *Phyllostachys Moso; Phyllostachys Atrovaginata; Dendrocalamus Asper*; or *Guadua Angustifolia*.

50. A media for transitioning shoots to ex vitro conditions wherein media comprises, consists essentially of or consists of Br-2-i media, Br-2-ii media, Br-2-iii media, Br-2-iv media, Br-2-v media, Ech-i media, Ech-ii media, Ech-iii media, Ech-iv, Ech-v media, Amel-i media, Amel-ii media, Amel-iii media, Amel-iv media or Amel-v media.

51. A media for micropropagating bamboo wherein said media comprises thidiazuron or an analogue thereof and supports 10-120 day multiplication cycles for at least six months.

52. A media according to embodiment 51 wherein said media supports 10-120 day multiplication cycles for at least one year.

53. A media according to embodiment 51 or 52 wherein said thidiazuron or analogue thereof is present in an amount from 0.0001 mg/mL-5 mg/mL.

54. A media according to embodiment 51, 52, or 53 wherein said media further comprises meta-topolin or an analogue thereof, NAA, BAP, 2ip and/or IBA.

55. A media according to embodiment 54, wherein said meta-topolin or analogue thereof is present in an amount from 0.0125 mg/mL-10 mg/mL.

56. A media according to embodiment 43, 44, 45, 46, 47, 51, 52, 53, 54 or 55 wherein said media comprises, consists essentially of or consists of b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

57. A method of micropropagating bamboo comprising culturing bamboo explants and/or shoots in a media of embodiment 51, 52, 53, 54, or 55.

58. A method of micropropagating bamboo according to embodiment 57 wherein said bamboo is *Phyllostachys bissetti; Fargesia denudata; Pleioblastus fortunei; Sasa Veitchii; Pleioblastus viridistriatus; Thamnocalamus crassinodus; Chusquea Culeo* "Cana Prieta"; *Bambusa Old Hamii; Phyllostachys Moso; Phyllostachys Atrovaginata; Dendrocalamus Asper;* or *Guadua Angustifolia.*

59. A kit comprising a media according to any one of embodiments 43, 44, 45, 46, 47, 50, 51, 52, 53, 54, 55, or 56.

Embodiments also include all of the embodiments provided above wherein the bamboo is that is micropropagated is *Arundinaria gigantea; Bambusa balcoa; Bambusa vulgaris; Bambusa vulgaris* 'Vitatta'; *Bambusa Oldhamii; Bambusa tulda; endrocalamus brandesii; Dendrocalamus asper; Dendrocalamus hamiltoni; Dendrocalamus giganteus; Dendrocalamus membranaceus; Dendrocalamus strictus; Gigantochloa aspera; Gigantochloa scortechini; Guadua culeata; uadua aculeata* 'Nicaragua'; *Guadua amplexifolia; Guadua angustifolia; Guadua angustofolia* bi-color; *Guadua paniculata; Melocanna bambusoides; eohouzeaua dullooa* (Teinostachyum); *Ochlandra travancorica; Phyllostachys edulis* 'Moso'; *Phyllostachys nigra; Phyllostachys nigra* 'Henon'; or *Schizostachyum lumampao*.

DETAILED DESCRIPTION OF THE DISCLOSURE

Bamboos are versatile plants with many different applications. They are a staple of Asian cuisine and are found in a number of products including toothpicks, brooms, poles for viticulture and arboriculture, landscaping materials, parquet flooring, laminate materials, furniture, handicrafts and other household items. In addition, bamboo is becoming an important source of textile material as a component of paper production and as a source of structural timber.

Bamboo is considered an environmentally friendly "green" product. One of the characteristics that gives bamboo its green reputation is its extremely rapid growth rate. Despite bamboo's rapid growth rate, however, it has other characteristics that make it a difficult crop to manage including its long flowering cycle and tendency to exhibit mass (or gregarious) flowering.

Embodiments disclosed herein provide for the micropropagation or tissue culturing (these terms are used interchangeably herein) of bamboo on a commercial scale.

Micropropagated plants are grown in vitro in sterile media. The sterile media can be liquid, semi-solid, or solid, and the physical state of the media can be varied by the incorporation of one or more gelling agents. Any gelling agent known in the art that is suitable for use in plant tissue culture media can be used. Agar is most commonly used for this purpose. Examples of such agars include Agar Type A, E or M and Bacto™Agar. Other exemplary gelling agents include carrageenan, gellan gum (commercially available as PhytaGel™, Gelrite® and Gelzan™), alginic acid and its salts, and agarose. Blends of these agents, such as two or more of agar, carrageenan, gellan gum, agarose and alginic acid or a salt thereof also can be used. Typically, the media comprises agar, with the addition of various compounds such as nutrients, inorganic salts, growth regulators, sugars, vitamins and other compounds. Other media additives can include, but are not limited to, amino acids, macroelements, iron, microelements, inositol and undefined media components such as casein hydrolysates or yeast extracts. For example, the media can include any combination of $NH_4NO_3$; $KNO_3$; $Ca(NO_3)_2$; $K_2SO_4$; $MgSO_4$; $MnSO_4$; $ZnSO_4$; $CuSO_4$; $CaCl_2$; KI; $CoCl_2$; $H_3BO_3$; $Na_2MoO_4$; $KH_2PO_4$; $FeSO_4$; $Na_2EDTA$; $Na_2H_2PO_4$; myo-inositol; thiamine; pyridoxine; nicotinic acid; glycine; riboflavin; ascorbic acid; silicon standard solution; β-naphthoxyacetic acid (NAA); indole butyric acid (IBA); 3-indoleacetic acid (IAA); benzylaminopurine (BAP); 6-γ-γ-(dimethylallylamino)-purine (2-ip); sugar; agar; carrageenan and charcoal. Examples of plant growth regulators include auxins and compounds with auxin-like activity, cytokinins and compounds with cytokinin-like activity. Exemplary auxins include 2,4-dichlorophenoxyacetic acid, IBA, picloram and combinations thereof. Exemplary cytokinins, in addition to meta-topolin and thidiazuron, include adenine hemisulfate, benzyladenine, dimethylallyladenine, kinetin, zeatin and combinations thereof. Gibberellic acid also can be included in the media. A sugar can be included in the media and can serve as a carbon source. Such sugars are known to those of ordinary skill in the art. Exemplary sugars include sucrose, glucose, maltose, galactose and sorbitol or combinations thereof.

Disclosed herein are specialized media, systems and methods that allow the successful tissue culturing of bamboo on a commercial scale. Certain media described herein include the cytokinins meta-topolin and/or thidiazuron. While certain embodiments utilize meta-topolin and/or thidiazuron defined as the particular compounds below, other related compounds can also be successful.

Compounds useful according to the present disclosure include meta-topolin analogues having a general formula

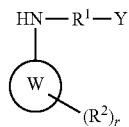

wherein W is an aryl or heteroaryl;
$R^1$ is substituted or unsubstituted alkyl wherein any C in the alkyl can be substituted with O, N or S;
each $R^2$ is independently H, OH, $C_1$-$C_6$ alkyl, $C_1$-$C_6$ alkylene, $C_1$-$C_6$ alkylyl, halogen, cyano, $C_1$-$C_6$ alkyloxy, aryl or heteroaryl each optionally substituted with a $C_1$-$C_6$ alkyl, SH, $NHR^3$, $CO_2R^3$ or halogen;
$R^3$ is H, OH, $C_1$-$C_6$ alkyl, $C_1$-$C_6$ alkylene, $C_1$-$C_6$ alkylyl, halogen, carboxylic group, ester group, aldehyde or cyano;
r is 0 to 8.

In one embodiment, W is

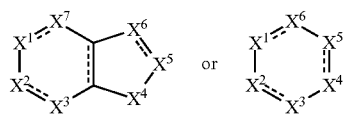

wherein a dashed line represents the presence or absence of a bond;
$X^1$-$X^7$ is each independently selected from C, N, O, S with the proviso that the X linking the ring to N is C.

In another embodiment, the compounds have a structure

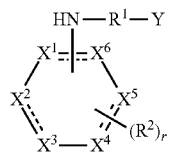

wherein a dashed line represents the presence or absence of a bond.

In another embodiment, the compounds have a structure

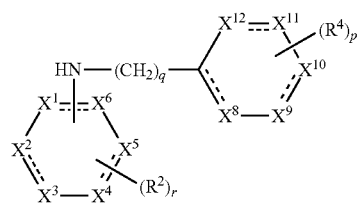

wherein a dashed line represents the presence or absence of a bond;
$X^8$-$X^{12}$ is each independently selected from C, N, O, S;
each $R^4$ is independently H, OH, $C_1$-$C_6$ alkyl, $C_1$-$C_6$ alkylene, $C_1$-$C_6$ alkylyl, halogen, cyano, $C_1$-$C_6$ alkyloxy, aryl or heteroaryl each optionally substituted with a $C_1$-$C_6$ alkyl, SH, $NHR^3$, $CO_2R^3$ or halogen;
$R^3$ is H, OH, $C_1$-$C_6$ alkyl, $C_1$-$C_6$ alkylene, $C_1$-$C_6$ alkylyl, halogen, carboxylic group, ester group, aldehyde or cyano;
p is 0 to 5; and
q is 0 to 6.

In other embodiments, the compounds have a structure

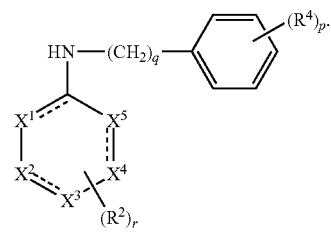

In still another embodiment, the compounds have a structure

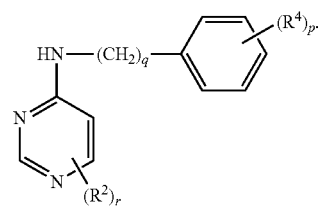

Further still, compounds can have structures selected from

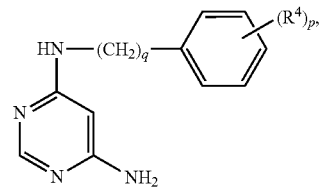

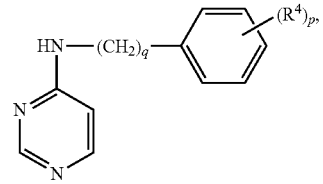

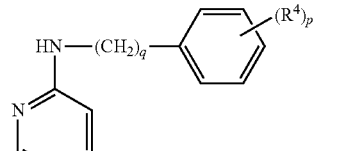

or

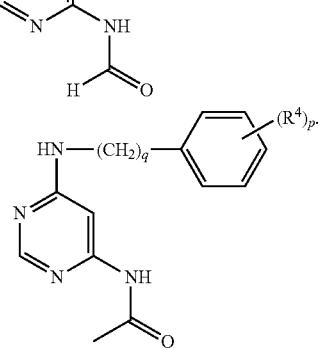

In one embodiment, $R^4$ is OH.

In another embodiment, compounds have a structure selected from

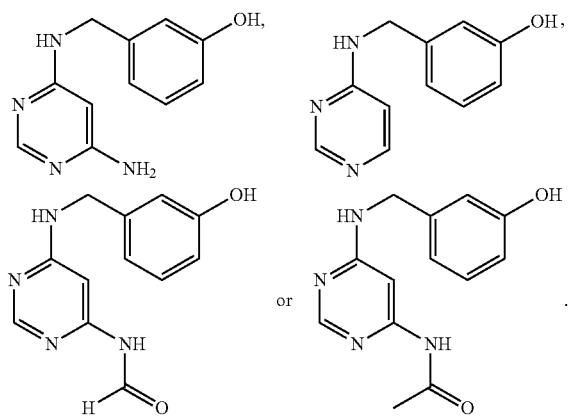

In another embodiment, the compounds have a structure

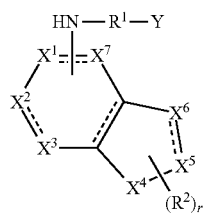

wherein a dashed line represents the presence or absence of a bond.

In another embodiment, the compounds have a structure

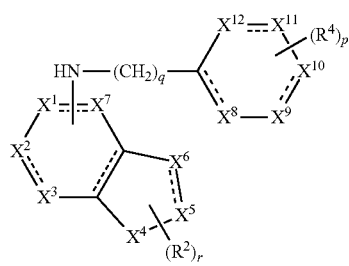

wherein a dashed line represents the presence or absence of a bond;

$X^8$-$X^{12}$ is each independently selected from C, N, O, S;

each $R^4$ is independently H, OH, $C_1$-$C_6$ alkyl, $C_1$-$C_6$ alkylene, $C_1$-$C_6$ alkylyl, halogen, cyano, $C_1$-$C_6$ alkyloxy, aryl or heteroaryl each optionally substituted with a $C_1$-$C_6$ alkyl, SH, $NHR^3$, $CO_2R^3$ or halogen;

$R^3$ is H, OH, $C_1$-$C_6$ alkyl, $C_1$-$C_6$ alkylene, $C_1$-$C_6$ alkylyl, halogen, carboxylic group, ester group, aldehyde or cyano;

p is 0 to 5; and q is 0 to 6.

In other embodiments, the compounds have a structure

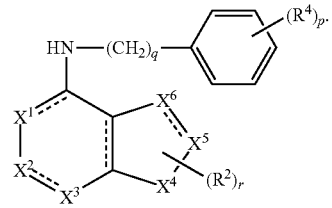

In still another embodiment, the compounds have a structure

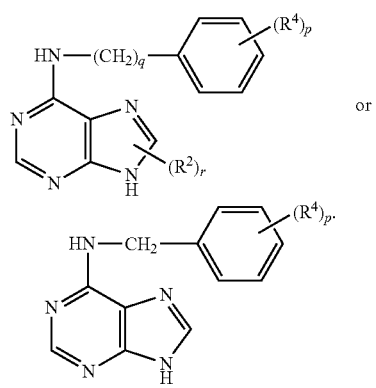

In one embodiment, the compound is meta-topolin, also known as 6-(3-hydroxybenzylamino)-purine, and by the abbreviation mT, having a molecular formula of $C_{12}H_{10}N_5OH$, a molecular weight of 241.25, and the following structural formula:

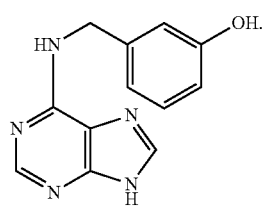 [SMILES: Oc1cccc(CNc2ncnc3[nH]cnc23)c1]

wherein said meta-topolin is a derivative of a willow tree or a poplar tree.

Compounds useful according to the present disclosure include thiadiazuron analogues having a general formula

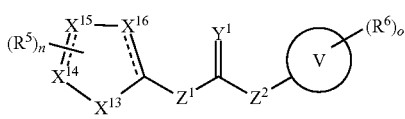

wherein V is an aryl or heteroaryl;

each $R^5$ and $R^6$ is each independently H, OH, $C_1$-$C_6$ alkyl, $C_1$-$C_6$ alkylene, $C_1$-$C_6$ alkylyl, halogen, cyano, $C_1$-$C_6$ alkyloxy, aryl or heteroaryl each optionally substituted with a $C_1$-$C_6$ alkyl or halogen;

n is 0 to 4;

o is 0 to 5

$X^{13}$-$X^{16}$ is each independently selected from C, N, O, S;

$Z^1$ and $Z^2$ are each independently NH, O, SH or CH or $Z^1$ and $Z^2$ can be combined to form a substituted or unsubstituted aryl or heteroaryl; and $Y^1$ is O or S.

In another embodiment, compounds have a structure

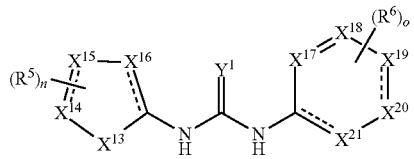

wherein $X^{17}$-$X^{21}$ is each independently selected from C, N, O, S.

In other embodiments, compounds include

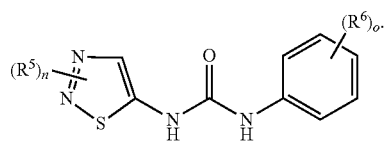

In one embodiment, the compound is Thidiazuron, also known as 1-phenyl-3-(1,2,3-thiadiazol-5-yl)urea and 5-phenylcarbamoylamino-1,2,3-thiadiazole has the molecular formula of $C_9H_8N_4OS$, a molecular weight of 220.25 and the following structural formula

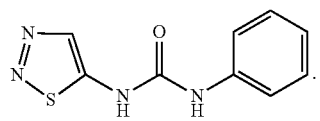 [SMILES: O=C(Nc1ccccc1)Nc1cnns1]

If present in a media, each cytokinin can be present in an amount from 0.001 mg/L-100 mg/L and all amounts in between. In certain embodiments, meta-topolin and/or its analogues can be present at 0.001 mg/L, 0.01, 0.1, 1, 2, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/L. In particular embodiments, thidiazuron and/or its analogues can be present at 0.001 mg/L, 0.01, 0.025, 0.05, 0.075, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.25, 1.50, 1.75, 2.25, 2.5, 2.75, 3.5, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/L.

When both are utilized, meta-topolin and/or its analogues and thidiazuron and/or its analogues can also be included in ratios. For example, the amount of meta-topolin and/or its analogues to thidiazuron and/or its analogues can be 100:1, 95:1, 90:1, 85:1, 80:1, 75:1, 70:1, 65:1, 60:1, 55:1, 50:1, 45:1, 40:1, 35:1, 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1; 9:1, 8:1, 7:1, 6.9:1, 6.8:1, 6.7:1, 6.6:1, 6.5:1, 6.4:1, 6.3:1, 6.2:1, 6.1:1, 6:1, 5.9:1, 5.8:1, 5.7:1, 5.6:1, 5.5:1, 5.4:1, 5.3:1, 5.2:1, 5.1:1, 5:1; 4:1, 3:1, 2:1, 1:1, 0.75:1, 0.5:1, 0.25:1, 0.1:1, 0.075:1, 0.05:1, 0.025:1 or 0.001:1. When both meta-topolin and thidiazuron are used, they can be present in the same or different media.

NAA, BAP, 2ip and/or IBA can similarly can be present at 0.001 mg/L, 0.01, 0.1, 1, 2, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/L or 0.001 mg/L, 0.01, 0.025, 0.05, 0.075, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.25, 1.50, 1.75, 2.25, 2.5, 2.75, 3.5, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/L.

The structures or formula for a number of chemical compounds, including meta-topolin and thidiazuron, have been provided above. One of ordinary skill in the art will recognize reference to a compound should be construed broadly to include pharmaceutically acceptable salts, prodrugs, tautomers, alternate solid forms, non-covalent complexes, analogs, derivatives and combinations thereof, of a chemical entity of the depicted structure or chemical name.

A pharmaceutically acceptable salt is any salt of the parent compound that is suitable for use in the methods disclosed herein. A pharmaceutically acceptable salt also refers to any salt which may form as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

Not intended to be limited by the above described compounds, various tautomers of the above compounds may be possible. As used herein, "tautomer" refers to the migration of protons between adjacent single and double bonds. The tautomerization process is reversible. Other tautomers are possible when the compound includes, for example but not limited to, enol, keto, lactamin, amide, imidic acid, amine, and imine groups. Tautomers will generally reach an equilibrium state wherein the double bond is resonantly shared between the two bond lengths.

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

As an overview, in typical micropropagation, plants are placed in various media that stimulate physiological processes such as growth and multiplication by and/or within the plant. Generally the process includes 3 steps (following explant preparation and disinfection, discussed below): (1) initiation of in vitro growth and/or multiplication of the explant in a media; (2) further in vitro multiplication in a second media; and (3) transition to ex vitro conditions. Not every tissue culture process requires each step, however, and in certain processes, steps can be combined or skipped. For example, while there is commonly a change in media types between steps 1 and 2, in certain embodiments, a media change is not included. In other processes, plants may not require a particular step promoting transition to ex vitro conditions but instead complete the process in a same media that supports multiplication. Accordingly, as described herein, media are defined as Stage 1 media ($1^{st}$ media of a process); Stage 2 media ($2^{nd}$ media of a process); Stage 3 media ($3^{rd}$ media of a process); etc. Particular media can change stage based on the number of steps within a particular process and where the particular media resides within their order.

To begin the process, a Stage 1 media can be obtained or prepared. Stage 1 media include a pH that is generally hospitable to plants (typically from 4.0-7.0 or 4.5-6.5). The Stage 1 media is then placed into test tubes or other appropriate containers (including jars, boxes, jugs, cups, etc. wherein when not specified are collectively referred to as "tubes"). These tubes can be capped or covered and autoclaved to sterilize the tubes and media. In another embodiment, sterilization is achieved by autoclaving at 5-25 pounds pressure psi at a temperature of 200° F.—for 200° F. 10-25 minutes. In another embodiment, sterilization is achieved by autoclaving at 15 pounds pressure psi at a temperature of 250° F. for 15-18 minutes. Sterility can also be assessed by an accepted number of contaminated tubes per hundred tubes, for example and without limitation, 0 contaminated tubes per hundred tubes, no more than 1 contaminated tube per hundred tubes, no more than 2 contaminated tubes per hundred tubes, no more than 3 contaminated tubes per hundred tubes, no more than 4 contaminated tubes per hundred tubes, no more than 5 contaminated tubes per hundred tubes, no more than 6 contaminated tubes per hundred tubes, no more than 7 contaminated tubes per hundred tubes, no more than 8 contaminated tubes per hundred tubes, no more than 9 contaminated tubes per hundred tubes, no more than 10 contaminated tubes per hundred tubes, etc.

In media containing a gelling agent, such as agar, agarose, gellan gum, carrageenan or combinations thereof, the media solidifies upon cooling and serves to provide the micropropagated plant tissues with support, nutrients, growth regulators, water and other compounds as described below. Generally, tubes and jars contain 15-25 mL media while boxes contain 40-50 mL media. Cups can include 30-40 mL while jugs generally contain more than 50 mL.

Micropropagated plants begin from a selected piece of plant tissue, called an "explant" or "mother plant." This explant is the source of cells to be developed during the tissue culturing process. The explant can be any segment or collection of cells from apical meristem, axillary buds, cambium, lateral meristem, shoot apices, stem segments, immature nodal sections from stems, lateral shoots, seedlings or leaf segments. In one embodiment, the explant is taken from a 1 year old bamboo plant. In another embodiment, the explant is taken from a 2 year old bamboo plant. In another embodiment, the explant is taken from a bamboo plant that is 5 years old or less. In another embodiment, the explant is taken from a bamboo plant that is 4 years old or less. In another embodiment, the explant is taken from a bamboo plant that is 3 years old or less. In another embodiment, the explant is taken from a bamboo plant that is 2 years old or less. In another embodiment, the explant is taken from a bamboo plant that is 1 years old or less. In another embodiment, the explant is taken from a bamboo plant that is 6 months old or less. In another embodiment, the explant is taken from a bamboo plant that is 3 months old or less. The bamboo from which the explant is obtained can be grown in any suitable husbandry situation, including but not limited to growing in a growth chamber, growing in a greenhouse or growing in a field.

As will be understood by one of ordinary skill in the art, a variety of appropriate explants can be used in accordance with the present disclosure. In certain embodiments according to the present disclosure, immature nodal sections from stems can be used as the explant material. In one embodiment, the explants can be new growth canes with the lateral shoots just breaking the sheath at nodal section(s). New growth canes include those obtained from the plant within a current season or year, wherein such new growth canes can be obtained from any node on the plant. In one particular embodiment, explant material includes or is limited to the third node from the base of a cane.

Nodal section(s) can be cut into 3-5, 1-10, 2-9, 3-8, 4-6, 3-6 or 2-7 millimeter sections with the shoot intact and disinfected to remove pathogens on the exterior of the explant. Any disinfection method known in the art can be used. Exemplary disinfection methods include application of a disinfectant, such as a disinfectant selected from among bleach (sodium and/or potassium and/or calcium hypochlorite), alcohol (e.g., ethanol, isopropyl), ozone, chlorine gas, iodine solution or antibiotic or anti-fungal solution or combinations thereof, or subjecting the exposed surface of the explant to ultraviolet light or to a temperature of −20° C. or lower or to a temperature higher than 40° C. or 50° C. for a short period of time. In certain embodiments, small amounts (a few drops) of Tween 20 can be added to the disinfecting solutions.

Following initial disinfection, the outer sheaths can be peeled off and discarded and the remaining piece put into an approximately 1%, 5%, 10%, 15%, 20%, 25% or 30% solution of a commercial bleach or a similar disinfecting solution. The peeled explant in disinfecting solution can be put onto a shaker table, such as for example, a Lab Rotators, Adjustable speed, Barnstead/Lab line orbital Shaker (model number KS 260) for 10 minutes, 20 minutes, 30 minutes, 60 minutes, 90 minutes, 120 minutes, 150 minutes, 180 minutes or 210 minutes at 6-9 or 1, 2, 3, 4, 5, 6, 7, 8, 9, 10, 11 or 12, 13, 14, or 15 revolutions per minute. In another embodiment, the peeled explants can then be put into an approximately 1% solution of bleach or similar disinfecting solution, and placed back onto the shaker table for 30 minutes. In another embodiment, this 1% bleach or similar disinfecting solution step can be repeated. In another embodiment, these described steps are progressive and include the entire disinfection process. As will be understood by one of ordinary skill in the art, a variety of appropriate disinfecting procedures can be used in accordance with the present disclosure.

Once disinfected, the explants can be placed onto a Stage 1 media within the tube and the tubes can be placed in a regulated growth chamber. As used herein, "growth chambers" can include a number of configurations and sizes including table-top boxes, stand-alone chambers, closets, small rooms, large rooms, etc. As is understood by one of ordinary skill in the art, variables such as light or temperature can be appropriately controlled in such a growth chamber. Appropriate ranges for tissue culturing bamboo include from 65° F.-70° F., 60° F.-75° F. or 55° F.-80° F. at 200-500, 150-550 or 100-600 foot candles. Lighting can be full spectrum, although alternative lighting systems can also be utilized according to the present disclosure.

The explants are allowed to establish themselves within the tubes while in the growth chamber on Stage 1 media. In more common 3 stage tissue culturing, once established (i.e. growing without visible contamination), the cell cultures grown from the explants are transferred into a second, Stage 2 media. Alternatively, once established, the cell cultures can remain in Stage 1 media. At this stage in the tissue culturing process, a large number of plants can be created within a relatively short period of time because each cell culture can develop multiple shoots and each shoot can be separated and placed into an individual tube where it will develop additional shoots to separate and multiply.

Without limiting the media to a particular stage, non-limiting examples of media that commonly serve as Stage 1 and/or Stage 2 media include:

Media b-12c(i-v):

| Component (mg/L in all unless otherwise noted) | b-12c-i | b-12c-ii | b-12c-iii | b-12c-iv | b-12c-v |
|---|---|---|---|---|---|
| $NH_4NO_3$ | 825-2475 | 1237-2063 | 1485-1815 | 1650 | 1650 ± 2 |
| $KNO_3$ | 950-2850 | 1425-2375 | 1710-2090 | 1900 | 1900 ± 2 |
| $Ca(NO_3)_2$ | 225-775 | 410-690 | 495-605 | 550 | 550 ± 2 |
| $MgSO_4$ | 185-555 | 275-465 | 330-410 | 370 | 370 ± 2 |
| $MnSO_4$ | 8.0-26.0 | 12.0-22.0 | 15.0-19.0 | 16.9 | 16.9 ± 0.2 |
| $ZnSO_4$ | 4.0-12.0 | 6.0-10.0 | 8.0-9.0 | 8.6 | 8.6 ± 0.2 |
| $CuSO_4$ | 0.012-0.378 | 0.020-0.030 | 0.022-0.028 | 0.025 | 0.025 ± .002 |
| $CaCl_2$ | 220-660 | 330-350 | 400-480 | 440 | 440 ± 2 |
| KI | 0.40-1.25 | 0.60-1.05 | 0.75-0.90 | 0.83 | 0.83 ± .02 |
| $CoCl_2$ | 0.012-0.378 | 0.020-0.030 | 0.022-0.028 | 0.025 | 0.025 ± .002 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 85-255 | 120-210 | 150-190 | 170 | 170 ± 2 |
| myo-Inositol | 50-150 | 75-125 | 90-110 | 100 | 100 ± 2 |
| Thiamine | 0.2-0.6 | 0.3-0.5 | 0.36-0.44 | 0.4 | 0.4 ± 0.2 |
| NAA | 0.02-0.08 | 0.03-0.07 | 0.04-0.06 | 0.05 | 0.05 ± .02 |
| BAP | 0.5-1.5 | 0.7-1.3 | 0.9-1.1 | 1 | 1 ± 0.2 |
| Thidiazuron | 0.36-1.12 | 0.56-0.94 | 0.67-.083 | 0.75 | 0.75 ± .02 |
| Meta-topolin | 2.5-7.5 | 3.7-6.2 | 4.5-5.5 | 5 | 5 ± 2 |
| Sugar g/L | 15-45 | 22-37 | 27-33 | 30 | 30 ± 2 |
| Agar g/L | 2.7-8.2 | 4.1-6.8 | 4.9-6.1 | 5.5 | 5.5 ± 0.2 |

Media CW2(i-v):

| Component | CW2-i | CW2-ii | CW2-iii | CW2-iv | CW2-v |
|---|---|---|---|---|---|
| $NH_4NO_3$ | 825-2475 | 1237-2063 | 1485-1815 | 1650 | 1650 ± 2 |
| $KNO_3$ | 950-2850 | 1425-2375 | 1710-2090 | 1900 | 1900 ± 2 |
| $Ca(NO_3)_2$ | 225-775 | 410-690 | 495-605 | 550 | 550 ± 2 |
| $MgSO_4$ | 185-555 | 275-465 | 330-410 | 370 | 370 ± 2 |
| $MnSO_4$ | 8.0-26.0 | 12.0-22.0 | 15.0-19.0 | 16.9 | 16.9 ± 0.2 |
| $ZnSO_4$ | 4.0-12.0 | 6.0-10.0 | 8.0-9.0 | 8.6 | 8.6 ± 0.2 |
| $CuSO_4$ | 0.012-0.378 | 0.020-0.030 | 0.022-0.028 | 0.025 | 0.025 ± .002 |
| $CaCl_2$ | 220-660 | 330-350 | 400-480 | 440 | 440 ± 2 |
| KI | 0.40-1.25 | 0.60-1.05 | 0.75-0.90 | 0.83 | 0.83 ± .02 |
| $CoCl_2$ | 0.012-0.378 | 0.020-0.030 | 0.022-0.028 | 0.025 | 0.025 ± .002 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 85-255 | 120-210 | 150-190 | 170 | 170 ± 2 |
| myo-Inositol | 50-150 | 75-125 | 90-110 | 100 | 100 ± 2 |
| Thiamine | 0.2-0.6 | 0.3-0.5 | 0.36-0.44 | 0.4 | 0.4 ± 0.2 |
| NAA | 0.02-0.08 | 0.03-0.07 | 0.04-0.06 | 0.05 | 0.05 ± .02 |
| BAP | 0.5-1.5 | 0.7-1.3 | 0 9-1.1 | 1 | 1 ± 0.2 |
| Meta-topolin | 2.5-7.5 | 3.7-6.2 | 4.5-5.5 | 5 | 5 ± 2 |
| Sugar g/L | 15-45 | 22-37 | 27-33 | 30 | 30 ± 2 |
| Agar g/L | 2.7-8.2 | 4.1-6.8 | 4.9-6.1 | 5.5 | 5.5 ± 0.2 |

Media CW3(i-v):

| Component | CW3-i | CW3-ii | CW3-iii | CW3-iv | CW3-v |
|---|---|---|---|---|---|
| $NH_4NO_3$ | 825-2475 | 1237-2063 | 1485-1815 | 1650 | 1650 ± 2 |
| $KNO_3$ | 950-2850 | 1425-2375 | 1710-2090 | 1900 | 1900 ± 2 |
| $Ca(NO_3)_2$ | 225-775 | 410-690 | 495-605 | 550 | 550 ± 2 |
| $MgSO_4$ | 185-555 | 275-465 | 330-410 | 370 | 370 ± 2 |
| $MnSO_4$ | 8.0-26.0 | 12.0-22.0 | 15.0-19.0 | 16.9 | 16.9 ± 0.2 |
| $ZnSO_4$ | 4.0-12.0 | 6.0-10.0 | 8.0-9.0 | 8.6 | 8.6 ± 0.2 |
| $CuSO_4$ | 0.012-0.378 | 0.020-0.030 | 0.022-0.028 | 0.025 | 0.025 ± .002 |
| $CaCl_2$ | 220-660 | 330-350 | 400-480 | 440 | 440 ± 2 |
| KI | 0.40-1.25 | 0.60-1.05 | 0.75-0.90 | 0.83 | 0.83 ± .02 |
| $CoCl_2$ | 0.012-0.378 | 0.020-0.030 | 0.022-0.028 | 0.025 | 0.025 ± .002 |

| Component | CW3-i | CW3-ii | CW3-iii | CW3-iv | CW3-v |
|---|---|---|---|---|---|
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 85-255 | 120-210 | 150-190 | 170 | 170 ± 2 |
| myo-Inositol | 50-150 | 75-125 | 90-110 | 100 | 100 ± 2 |
| Thiamine | 0.2-0.6 | 0.3-0.5 | 0.36-0.44 | 0.4 | 0.4 ± 0.2 |
| NAA | 0.05-0.15 | 0.07-0.12 | 0.09-0.11 | 0.1 | 0.1 ± 0.02 |
| BAP | 0.5-1.5 | 0.7-1.3 | 0.9-1.1 | 1 | 1 ± 0.2 |
| IBA | 0.1-0.3 | 0.15-0.25 | 0.17-0.22 | 0.2 | 0.2 ± 0.1 |
| Meta-topolin | 2.5-7.5 | 3.7-6.2 | 4.5-5.5 | 5 | 5 ± 2 |
| Sugar g/L | 15-45 | 22-37 | 27-33 | 30 | 30 ± 2 |
| Agar g/L | 2.7-8.2 | 4.1-6.8 | 4.9-6.1 | 5.5 | 5.5 ± 0.2 |

Media b-9(i-v):

| Component | b-9-i | b-9-ii | b-9-iii | b-9-iv | b-9-v |
|---|---|---|---|---|---|
| $NH_4NO_3$ | 825-2475 | 1237-2063 | 1485-1815 | 1650 | 1650 ± 2 |
| $KNO_3$ | 950-2850 | 1425-2375 | 1710-2090 | 1900 | 1900 ± 2 |
| $MgSO_4$ | 185-555 | 275-465 | 330-410 | 370 | 370 ± 2 |
| $MnSO_4$ | 8.0-26.0 | 12.0-22.0 | 15.0-19.0 | 16.9 | 16.9 ± 0.2 |
| $ZnSO_4$ | 4.0-12.0 | 6.0-10.0 | 8.0-9.0 | 8.6 | 8.6 ± 0.2 |
| $CuSO_4$ | 0.012-0.378 | 0.020-0.030 | 0.022-0.028 | 0.025 | 0.025 ± .002 |
| $CaCl_2$ | 220-660 | 330-350 | 400-480 | 440 | 440 ± 2 |
| KI | 0.40-1.25 | 0.60-1.05 | 0.75-0.90 | 0.83 | 0.83 ± .02 |
| $CoCl_2$ | 0.012-0.378 | 0.020-0.030 | 0.022-0.028 | 0.025 | 0.025 ± .002 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 85-255 | 120-210 | 150-190 | 170 | 170 ± 2 |
| myo-Inositol | 50-150 | 75-125 | 90-110 | 100 | 100 ± 2 |
| Thiamine | 0.2-0.6 | 0.3-0.5 | 0.36-0.44 | 0.4 | 0.4 ± 0.2 |
| NAA | 0.02-0.08 | 0.03-0.07 | 0.04-0.06 | 0.05 | 0.05 ± .02 |
| BAP | 0.5-1.5 | 0.7-1.3 | 0.9-1.1 | 1 | 1 ± 0.2 |
| Thidiazuron | 0.12-0.36 | 0.18-0.31 | .22-.28 | 0.25 | 0.25 ± .02 |
| Meta-topolin | 2.5-7.5 | 3.7-6.2 | 4.5-5.5 | 5 | 5 ± 2 |
| Sugar g/L | 15-45 | 22-37 | 27-33 | 30 | 30 ± 2 |
| Agar g/L | 2.7-8.2 | 4.1-6.8 | 4.9-6.1 | 5.5 | 5.5 ± 0.2 |

Media CW4(i-v):

| Component | CW4-i | CW4-ii | CW4-iii | CW4-iv | CW4-v |
|---|---|---|---|---|---|
| $NH_4NO_3$ | 825-2475 | 1237-2063 | 1485-1815 | 1650 | 1650 ± 2 |
| $KNO_3$ | 950-2850 | 1425-2375 | 1710-2090 | 1900 | 1900 ± 2 |
| $MgSO_4$ | 185-555 | 275-465 | 330-410 | 370 | 370 ± 2 |
| $MnSO_4$ | 8.0-26.0 | 12.0-22.0 | 15.0-19.0 | 16.9 | 16.9 ± 0.2 |
| $ZnSO_4$ | 4.0-12.0 | 6.0-10.0 | 8.0-9.0 | 8.6 | 8.6 ± 0.2 |
| $CuSO_4$ | 0.012-0.378 | 0.020-0.030 | 0.022-0.028 | 0.025 | 0.025 ± .002 |
| $CaCl_2$ | 220-660 | 330-350 | 400-480 | 440 | 440 ± 2 |
| KI | 0.40-1.25 | 0.60-1.05 | 0.75-0.90 | 0.83 | 0.83 ± .02 |
| $CoCl_2$ | 0.012-0.378 | 0.020-0.030 | 0.022-0.028 | 0.025 | 0.025 ± .002 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 85-255 | 120-210 | 150-190 | 170 | 170 ± 2 |
| myo-Inositol | 50-150 | 75-125 | 90-110 | 100 | 100 ± 2 |
| Thiamine | 0.2-0.6 | 0.3-0.5 | 0.36-0.44 | 0.4 | 0.4 ± 0.2 |
| NAA | 0.05-0.15 | 0.07-0.12 | 0.09-0.11 | 0.1 | 0.1 ± 0.02 |
| BAP | 0.5-1.5 | 0.7-1.3 | 0.9-1.1 | 1 | 1 ± 0.2 |
| IBA | 0.1-0.3 | 0.15-0.25 | 0.17-0.22 | 0.2 | 0.2 ± 0.1 |
| Thidiazuron | 0.12-0.36 | 0.18-0.31 | .22-.28 | 0.25 | 0.25 ± .02 |
| Meta-topolin | 2.5-7.5 | 3.7-6.2 | 4.5-5.5 | 5 | 5 ± 2 |
| Sugar g/L | 15-45 | 22-37 | 27-33 | 30 | 30 ± 2 |
| Agar g/L | 2.7-8.2 | 4.1-6.8 | 4.9-6.1 | 5.5 | 5.5 ± 0.2 |

Media CW1(i-v):

| Component | CW1-i | CW1-ii | CW1-iii | CW1-iv | CW1-v |
|---|---|---|---|---|---|
| $NH_4NO_3$ | 825-2475 | 1237-2063 | 1485-1815 | 1650 | 1650 ± 2 |
| $KNO_3$ | 950-2850 | 1425-2375 | 1710-2090 | 1900 | 1900 ± 2 |
| $MgSO_4$ | 185-555 | 275-465 | 330-410 | 370 | 370 ± 2 |
| $MnSO_4$ | 8.0-26.0 | 12.0-22.0 | 15.0-19.0 | 16.9 | 16.9 ± 0.2 |
| $ZnSO_4$ | 4.0-12.0 | 6.0-10.0 | 8.0-9.0 | 8.6 | 8.6 ± 0.2 |
| $CuSO_4$ | 0.012-0.378 | 0.020-0.030 | 0.022-0.028 | 0.025 | 0.025 ± .002 |
| $CaCl_2$ | 220-660 | 330-350 | 400-480 | 440 | 440 ± 2 |
| KI | 0.40-1.25 | 0.60-1.05 | 0.75-0.90 | 0.83 | 0.83 ± .02 |
| $CoCl_2$ | 0.012-0.378 | 0.020-0.030 | 0.022-0.028 | 0.025 | 0.025 ± .002 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 85-255 | 120-210 | 150-190 | 170 | 170 ± 2 |
| myo-Inositol | 50-150 | 75-125 | 90-110 | 100 | 100 ± 2 |
| Thiamine | 0.2-0.6 | 0.3-0.5 | 0.36-0.44 | 0.4 | 0.4 ± 0.2 |
| NAA | 0.02-0.08 | 0.03-0.07 | 0.04-0.06 | 0.05 | 0.05 ± .02 |
| BAP | 0.5-1.5 | 0.7-1.3 | 0.9-1.1 | 1 | 1 ± 0.2 |
| Meta-topolin | 2.5-7.5 | 3.7-6.2 | 4.5-5.5 | 5 | 5 ± 2 |
| Sugar g/L | 15-45 | 22-37 | 27-33 | 30 | 30 ± 2 |
| Agar g/L | 2.7-8.2 | 4.1-6.8 | 4.9-6.1 | 5.5 | 5.5 ± 0.2 |
| Silicon Solution mL | 0.5-1.5 | 0.7-1.3 | 0.9-1.1 | 1 | 1 ± 0.2 |

Media CW5(i-v):

| Component | CW5-i | CW5-ii | CW5-iii | CW5-iv | CW5-v |
|---|---|---|---|---|---|
| $NH_4NO_3$ | 825-2475 | 1237-2063 | 1485-1815 | 1650 | 1650 ± 2 |
| $KNO_3$ | 950-2850 | 1425-2375 | 1710-2090 | 1900 | 1900 ± 2 |
| $MgSO_4$ | 185-555 | 275-465 | 330-410 | 370 | 370 ± 2 |
| $MnSO_4$ | 8.0-26.0 | 12.0-22.0 | 15.0-19.0 | 16.9 | 16.9 ± 0.2 |
| $ZnSO_4$ | 4.0-12.0 | 6.0-10.0 | 8.0-9.0 | 8.6 | 8.6 ± 0.2 |
| $CuSO_4$ | 0.012-0.378 | 0.020-0.030 | 0.022-0.028 | 0.025 | 0.025 ± .002 |
| $CaCl_2$ | 220-660 | 330-350 | 400-480 | 440 | 440 ± 2 |
| KI | 0.40-125 | 0.60-1.05 | 0.75-0.90 | 0.83 | 0.83 ± .02 |
| $CoCl_2$ | 0.012-0.378 | 0.020-0.030 | 0.022-0.028 | 0.025 | 0.025 ± .002 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 85-255 | 120-210 | 150-190 | 170 | 170 ± 2 |
| myo-Inositol | 50-150 | 75-125 | 90-110 | 100 | 100 ± 2 |
| Thiamine | 0.2-0.6 | 0.3-0.5 | 0.36-0.44 | 0.4 | 0.4 ± 0.2 |
| NAA | 0.02-0.08 | 0.03-0.07 | 0.04-0.06 | 0.05 | 0.05 ± .02 |
| BAP | 0.5-1.5 | 0.7-1.3 | 0.9-1.1 | 1 | 1 ± 0.2 |
| IBA | 0.1-0.3 | 0.15-0.25 | 0.17-0.22 | 0.2 | 0.2 ± 0.1 |
| Meta-topolin | 2.5-7.5 | 3.7-6.2 | 4.5-5.5 | 5 | 5 ± 2 |
| Sugar g/L | 15-45 | 22-37 | 27-33 | 30 | 30 ± 2 |
| Agar g/L | 2.7-8.2 | 4.1-6.8 | 4.9-6.1 | 5.5 | 5.5 ± 0.2 |
| Silicon Solution mL | 0.5-1.5 | 0.7-1.3 | 0.9-1.1 | 1 | 1 ± 0.2 |

Media CW6(i-v):

| Component | CW6-i | CW6-ii | CW6-iii | CW6-iv | CW6-v |
|---|---|---|---|---|---|
| $NH_4NO_3$ | 825-2475 | 1237-2063 | 1485-1815 | 1650 | 1650 ± 2 |
| $KNO_3$ | 950-2850 | 1425-2375 | 1710-2090 | 1900 | 1900 ± 2 |
| $MgSO_4$ | 185-555 | 275-465 | 330-410 | 370 | 370 ± 2 |
| $MnSO_4$ | 8.0-26.0 | 12.0-22.0 | 15.0-19.0 | 16.9 | 16.9 ± 0.2 |
| $ZnSO_4$ | 4.0-12.0 | 6.0-10.0 | 8.0-9.0 | 8.6 | 8.6 ± 0.2 |
| $CuSO_4$ | 0.012-0.378 | 0.020-0.030 | 0.022-0.028 | 0.025 | 0.025 ± .002 |
| $CaCl_2$ | 220-660 | 330-350 | 400-480 | 440 | 440 ± 2 |
| KI | 0.40-1.25 | 0.60-1.05 | 0.75-0.90 | 0.83 | 0.83 ± .02 |
| $CoCl_2$ | 0.012-0.378 | 0.020-0.030 | 0.022-0.028 | 0.025 | 0.025 ± .002 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $K_2SO_5$ | 181.85-545.63 | 272.80-454.69 | 327.45-400.05 | 363.75 | 363.75 ± .02 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 85-255 | 120-210 | 150-190 | 170 | 170 ± 2 |
| myo-Inositol | 50-150 | 75-125 | 90-110 | 100 | 100 ± 2 |
| Thiamine | 0.2-0.6 | 0.3-0.5 | 0.36-0.44 | 0.4 | 0.4 ± 0.2 |
| NAA | 0.05-0.15 | 0.07-0.12 | 0.09-0.11 | 0.1 | 0.1 ± 0.02 |
| BAP | 0.5-1.5 | 0.7-1.3 | 0.9-1.1 | 1 | 1 ± 0.2 |
| IBA | 0.1-0.3 | 0.15-0.25 | 0.17-0.22 | 0.2 | 0.2 ± 0.1 |
| Meta-topolin | 2.5-7.5 | 3.7-6.2 | 4.5-5.5 | 5 | 5 ± 2 |
| Thidiazuron | 0.12-0.36 | 0.18-0.31 | .22-.28 | 0.25 | 0.25 ± .02 |
| Sugar g/L | 15-45 | 22-37 | 27-33 | 30 | 30 ± 2 |
| Agar g/L | 2.7-8.2 | 4.1-6.8 | 4.9-6.1 | 5.5 | 5.5 ± 0.2 |

Media b-10(i-v):

| Component | b-10-i | b-10-ii | b-10-iii | b-10-iv | b-10-v |
|---|---|---|---|---|---|
| $NH_4NO_3$ | 825-2475 | 1237-2063 | 1485-1815 | 1650 | 1650 ± 2 |
| $KNO_3$ | 950-2850 | 1425-2375 | 1710-2090 | 1900 | 1900 ± 2 |
| $MgSO_4$ | 185-555 | 275-465 | 330-410 | 370 | 370 ± 2 |
| $MnSO_4$ | 8.0-26.0 | 12.0-22.0 | 15.0-19.0 | 16.9 | 16.9 ± 0.2 |
| $ZnSO_4$ | 4.0-12.0 | 6.0-10.0 | 8.0-9.0 | 8.6 | 8.6 ± 0.2 |
| $CuSO_4$ | 0.012-0.378 | 0.020-0.030 | 0.022-0.028 | 0.025 | 0.025 ± .002 |
| $CaCl_2$ | 220-660 | 330-350 | 400-480 | 440 | 440 ± 2 |
| KI | 0.40-1.25 | 0.60-1.05 | 0.75-0.90 | 0.83 | 0.83 ± .02 |
| $CoCl_2$ | 0.012-0.378 | 0.020-0.030 | 0.022-0.028 | 0.025 | 0.025 ± .002 |

-continued

| Component | b-10-i | b-10-ii | b-10-iii | b-10-iv | b-10-v |
|---|---|---|---|---|---|
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 85-255 | 120-210 | 150-190 | 170 | 170 ± 2 |
| myo-Inositol | 50-150 | 75-125 | 90-110 | 100 | 100 ± 2 |
| Thiamine | 0.2-0.6 | 0.3-0.5 | 0.36-0.44 | 0.4 | 0.4 ± 0.2 |
| NAA | 0.02-0.08 | 0.03-0.07 | 0.04-0.06 | 0.05 | 0.05 ± .02 |
| BAP | 0.5-1.5 | 0.7-1.3 | 0.9-1.1 | 1 | 1 ± 0.2 |
| Meta-topolin | 2.5-7.5 | 3.7-6.2 | 4.5-5.5 | 5 | 5 ± 2 |
| Sugar g/L | 15-45 | 22-37 | 27-33 | 30 | 30 ± 2 |
| Agar g/L | 2.5-7.5 | 3.7-6.2 | 4.5-5.5 | 5 | 5 ± 2 |

Media b-11(i-v):

| Component | b-11-i | b-11-ii | b-11-iii | b-11-iv | b-11-v |
|---|---|---|---|---|---|
| $NH_4NO_3$ | 825-2475 | 1237-2063 | 1485-1815 | 1650 | 1650 ± 2 |
| $KNO_3$ | 950-2850 | 1425-2375 | 1710-2090 | 1900 | 1900 ± 2 |
| $MgSO_4$ | 185-555 | 275-465 | 330-410 | 370 | 370 ± 2 |
| $MnSO_4$ | 8.0-26.0 | 12.0-22.0 | 15.0-19.0 | 16.9 | 16.9 ± 0.2 |
| $ZnSO_4$ | 4.0-12.0 | 6.0-10.0 | 8.0-9.0 | 8.6 | 8.6 ± 0.2 |
| $CuSO_4$ | 0.012-0.378 | 0.020-0.030 | 0.022-0.028 | 0.025 | 0.025 ± .002 |
| $CaCl_2$ | 220-660 | 330-350 | 400-480 | 440 | 440 ± 2 |
| KI | 0.40-1.25 | 0.60-1.05 | 0.75-0.90 | 0.83 | 0.83 ± .02 |
| $CoCl_2$ | 0.012-0.378 | 0.020-0.030 | 0.022-0.028 | 0.025 | 0.025 ± .002 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 85-255 | 120-210 | 150-190 | 170 | 170 ± 2 |
| myo-Inositol | 50-150 | 75-125 | 90-110 | 100 | 100 ± 2 |
| Thiamine | 0.2-0.6 | 0.3-0.5 | 0.36-0.44 | 0.4 | 0.4 ± 0.2 |
| NAA | 0.02-0.08 | 0.03-0.07 | 0.04-0.06 | 0.05 | 0.05 ± .02 |
| BAP | 0.5-1.5 | 0.7-1.3 | 0.9-1.1 | 1 | 1 ± 0.2 |
| Thidiazuron | 0.2-0.8 | 0.3-0.7 | 0.4-0.6 | 0.5 | 0.5 ± 0.2 |
| Meta-topolin | 2.5-7.5 | 3.7-6.2 | 4.5-5.5 | 5 | 5 ± 2 |
| Sugar g/L | 15-45 | 22-37 | 27-33 | 30 | 30 ± 2 |
| Agar g/L | 2.7-8.2 | 4.1-6.8 | 4.9-6.1 | 5.5 | 5.5 ± 0.2 |

Media b-1(i-v):

| Component | b-1-i | b-1-ii | b-1-iii | b-1-iv | b-1-v |
|---|---|---|---|---|---|
| $NH_4NO_3$ | 600-1800 | 900-1500 | 1080-1320 | 1200 | 1200 ± 2 |
| $Ca(NO_3)_2$ | 838-2515 | 1257-2096 | 1510-1844 | 1677 | 1677 ± 2 |
| $K_2SO_4$ | 121-363 | 181-302 | 218-266 | 242 | 242 ± 2 |
| $MgSO_4$ | 270-830 | 410-690 | 500-610 | 555 | 555 ± 2 |
| $MnSO_4$ | 12.60-38.00 | 19.00-31.70 | 22.80-27.80 | 25.35 | 25.35 ± .02 |
| $ZnSO_4$ | 6.4-19.5 | 9.6-16.2 | 11.5-14.0 | 12.9 | 12.9 ± 0.2 |
| $CuSO_4$ | 0.018-0.055 | 0.027-0.046 | 0.033-0.041 | 0.037 | 0.037 ± 0.002 |
| $CaCl_2$ | 48-144 | 72-120 | 85-105 | 96 | 96 ± 2 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 42-128 | 63-106 | 75-95 | 85 | 85 ± 2 |
| myo-Inositol | 100-300 | 150-250 | 180-220 | 200 | 200 ± 2 |
| Thiamine | 0.4-1.4 | 0.6-1.1 | 0.8-1.0 | 0.9 | 0.9 ± 0.2 |
| Pyridoxine | 0.2-0.8 | 0.3-0.7 | 0.4-0.6 | 0.5 | 0.5 ± 0.2 |
| Nicotinic acid | 0.2-0.8 | 0.3-0.7 | 0.4-0.6 | 0.5 | 0.5 ± 0.2 |
| Glycine | 1-3 | 1.5-2.5 | 1.75-2.25 | 2 | 2 ± 1 |
| Riboflavin | 10-30 | 15-25 | 18-22 | 20 | 20 ± 2 |
| BAP | 0.1-0.3 | 0.15-0.25 | 0.17-0.22 | 0.2 | 0.2 ± 0.1 |
| NAA | 0.2-0.8 | 0.3-0.7 | 0.4-0.6 | 0.5 | 0.5 ± 0.2 |
| Thidiazuron | 0.36-1.12 | 0.56-0.94 | 0.67-.083 | 0.75 | 0.75 ± .02 |

-continued

| Component | b-1-i | b-1-ii | b-1-iii | b-1-iv | b-1-v |
|---|---|---|---|---|---|
| 2ip | 7-23 | 11-19 | 13-17 | 15 | 15 ± 2 |
| Sugar g/L | 15-45 | 22-37 | 27-33 | 30 | 30 ± 2 |
| Carrageenan g/L | 3-11 | 4-10 | 5-8 | 7 | 7 ± 2 |

Media b-4(i-v):

| Component | b-4-i | b-4-ii | b-4-iii | b-4-iv | b-4-v |
|---|---|---|---|---|---|
| $NH_4NO_3$ | 600-1800 | 900-1500 | 1080-1320 | 1200 | 1200 ± 2 |
| $Ca(NO_3)_2$ | 838-2515 | 1257-2096 | 1510-1844 | 1677 | 1677 ± 2 |
| $K_2SO_4$ | 121-363 | 181-302 | 218-266 | 242 | 242 ± 2 |
| $MgSO_4$ | 270-830 | 410-690 | 500-610 | 555 | 555 ± 2 |
| $MnSO_4$ | 12.60-38.00 | 19.00-31.70 | 22.80-27.80 | 25.35 | 25.35 ± .02 |
| $ZnSO_4$ | 6.4-19.5 | 9.6-16.2 | 11.5-14.0 | 12.9 | 12.9 ± 0.2 |
| $CuSO_4$ | 0.018-0.055 | 0.027-0.046 | 0.033-0.041 | 0.037 | 0.037 ± .002 |
| $CaCl_2$ | 48-144 | 72-120 | 85-105 | 96 | 96 ± 2 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 42-128 | 63-106 | 75-95 | 85 | 85 ± 2 |
| myo-Inositol | 100-300 | 150-250 | 180-220 | 200 | 200 ± 2 |
| Thiamine | 0.4-1.4 | 0.6-1.1 | 0.8-1.0 | 0.9 | 0.9 ± 0.2 |
| Pyridoxine | 0.2-0.8 | 0.3-0.7 | 0.4-0.6 | 0.5 | 0.5 ± 0.2 |
| Nicotinic acid | 0.2-0.8 | 0.3-0.7 | 0.4-0.6 | 0.5 | 0.5 ± 0.2 |
| Glycine | 1-3 | 1.5-2.5 | 1.75-2.25 | 2 | 2 ± 1 |
| Riboflavin | 10-30 | 15-25 | 18-22 | 20 | 20 ± 2 |
| BAP | 2.5-7.5 | 3.7-6.2 | 4.5-5.5 | 5 | 5 ± 2 |
| NAA | 0.5-1.5 | 0.7-1.3 | 0.9-1.1 | 1 | 1 ± 0.2 |
| Thidiazuron | 0.36-1.12 | 0.56-0.94 | 0.67-.083 | 0.75 | 0.75 ± .02 |
| 2ip | 10-30 | 15-25 | 18-22 | 20 | 20 ± 2 |
| Sugar g/L | 15-45 | 22-37 | 27-33 | 30 | 30 ± 2 |
| Carrageenan g/L | 3-11 | 4-10 | 5-8 | 7 | 7 ± 2 |

Media b-6(i-v):

| Component | b-6-i | b-6-ii | b-6-iii | b-6-iv | b-6-v |
|---|---|---|---|---|---|
| $NH_4NO_3$ | 600-1800 | 900-1500 | 1080-1320 | 1200 | 1200 ± 2 |
| $Ca(NO_3)_2$ | 838-2515 | 1257-2096 | 1510-1844 | 1677 | 1677 ± 2 |
| $K_2SO_4$ | 121-363 | 181-302 | 218-266 | 242 | 242 ± 2 |
| $MgSO_4$ | 270-830 | 410-690 | 500-610 | 555 | 555 ± 2 |
| $MnSO_4$ | 12.60-38.00 | 19.00-31.70 | 22.80-27.80 | 25.35 | 25.35 ± .02 |
| $ZnSO_4$ | 6.4-19.5 | 9.6-16.2 | 11.5-14.0 | 12.9 | 12.9 ± 0.2 |
| $CuSO_4$ | 0.018-0.055 | 0.027-0.046 | 0.033-0.041 | 0.037 | 0.037 ± .002 |
| $CaCl_2$ | 48-144 | 72-120 | 85-105 | 96 | 96 ± 2 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 27.0-84.0 | 40.0-70.0 | 50.0-60.0 | 55.7 | 55.7 ± 0.2 |
| $Na_2EDTA$ | 37.0-112.0 | 55.0-94.0 | 67.0-82.0 | 74.6 | 74.6 ± 0.2 |
| $Na_2H_2PO_4$ | 42-128 | 63-106 | 75-95 | 85 | 85 ± 2 |
| myo-Inositol | 100-300 | 150-250 | 180-220 | 200 | 200 ± 2 |
| Thiamine | 0.4-1.4 | 0.6-1.1 | 0.8-1.0 | 0.9 | 0.9 ± 0.2 |
| Pyridoxine | 0.2-0.8 | 0.3-0.7 | 0.4-0.6 | 0.5 | 0.5 ± 0.2 |
| Nicotinic acid | 0.2-0.8 | 0.3-0.7 | 0.4-0.6 | 0.5 | 0.5 ± 0.2 |
| Glycine | 1-3 | 1.5-2.5 | 1.75-2.25 | 2 | 2 ± 1 |
| Riboflavin | 10-30 | 15-25 | 18-22 | 20 | 20 ± 2 |
| NAA | 0.5-1.5 | 0.7-1.3 | 0.9-1.1 | 1 | 1 ± 0.2 |
| Thidiazuron | 0.12-0.36 | 0.18-0.31 | .22-.28 | 0.25 | 0.25 ± .02 |
| 2ip | 2.5-7.5 | 3.7-6.2 | 4.5-5.5 | 5 | 5 ± 2 |
| Sugar g/L | 12-37 | 15-35 | 20-30 | 25 | 25 ± 2 |
| Agar g/L | 2.7-8.2 | 4.1-6.8 | 4.9-6.1 | 5.5 | 5.5 ± 0.2 |
| Carrageenan g/L | 1-3 | 1.5-2.5 | 1.75-2.25 | 2 | 2 ± 1 |

Note that for each of these media, its solid form is provided. Each media can be transformed into a liquid media by removing agar or carageenan and liquid forms of these media and their uses are expressly included within the scope of the present disclosure.

The expected number of shoots may be different at different stages of the tissue culturing process and can also depend on the species of bamboo. In general, however, at the beginning of the process, multiplication is from 1.0-2.0, 1.0-3.0 or 2.0-3.0 times. Once established, multiplication can depend on the chosen container. For example, multiplication can range from, without limitation, 1-10 or 2-6 plants per tube, 1-15 or 4-9 plants per jar, 1-20 or 9-17 plants per box or 1-50 or 20-35 plants per jug. The number 1 is included because certain species or particular cell cultures require more time in Stage 1 or Stage 2 media before multiplication begins. By carrying them through the process, however, most if not all begin multiplication within a number of cycles. For example, some cell cultures may begin to multiply only after 1, 2, 3, 4, 5, 6, 7, 8, 9, 10, 11, 12, 13, 14, 15, 16, 17 or 18 months in culture.

Methods disclosed herein can produce the following non-limiting number of shoots from a single explant: 100, 500, 1,000; 5,000; 10,000, 20,000, 50,000, 100,000, 250,000, 500,000, 750,000, 1,000,000 or more.

Following multiplication through culturing and subculturing, particular plant shoots can be selected for transition to ex vitro conditions. Generally, media that support transition to ex vitro conditions represent a Stage 2, Stage 3, Stage 4 or Stage 5 media. Non-limiting examples of such media include: Media Ech(i-v):

| Component | Ech-i | Ech-ii | Ech-iii | Ech-iv | Ech-v |
|---|---|---|---|---|---|
| $NH_4NO_3$ | 825-2475 | 1237-2063 | 1485-1815 | 1650 | 1650 ± 2 |
| $KNO_3$ | 950-2850 | 1425-2375 | 1710-2090 | 1900 | 1900 ± 2 |
| $MgSO_4$ | 185-555 | 275-465 | 330-410 | 370 | 370 ± 2 |
| $MnSO_4$ | 8.0-26.0 | 12.0-22.0 | 15.0-19.0 | 16.9 | 16.9 ± 0.2 |
| $ZnSO_4$ | 4.0-12.0 | 6.0-10.0 | 8.0-9.0 | 8.6 | 8.6 ± 0.2 |
| $CuSO_4$ | 0.012-0.378 | 0.020-0.030 | 0.022-0.028 | 0.025 | 0.025 ± .002 |
| $CaCl_2$ | 220-660 | 330-350 | 400-480 | 440 | 440 ± 2 |
| KI | 0.40-1.25 | 0.60-1.05 | 0.75-0.90 | 0.83 | 0.83 ± .02 |
| $CoCl_2$ | 0.012-0.378 | 0.020-0.030 | 0.022-0.028 | 0.025 | 0.025 ± .002 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 85-255 | 120-210 | 150-190 | 170 | 170 ± 2 |
| $FeSO_4$ | 13.0-42.0 | 20.8-34.7 | 25.1-30.5 | 27.8 | 27.8 ± 0.2 |
| $Na_2EDTA$ | 18.6-56.0 | 28.0-46.6 | 33.6-41.0 | 37.3 | 37.3 ± 0.2 |
| myo-Inositol | 50-150 | 75-125 | 90-110 | 100 | 100 ± 2 |
| Thiamine | 0.2-0.6 | 0.3-0.5 | 0.35-0.45 | 0.4 | 0.4 ± 0.2 |
| Pyridoxine | 0.2-0.8 | 0.3-0.7 | 0.4-0.6 | 0.5 | 0.5 ± 0.2 |
| Nicotinic acid | 0.2-0.8 | 0.3-0.7 | 0.4-0.6 | 0.5 | 0.5 ± 0.2 |
| Glycine | 1-3 | 1.5-2.5 | 1.75-2.25 | 2 | 2 ± 1 |
| NAA | 0.05-0.15 | 0.07-0.12 | 0.09-0.11 | 0.1 | 0.1 ± 0.02 |
| IAA | 0.02-0.08 | 0.03-0.07 | 0.04-0.06 | 0.05 | 0.05 ± .02 |
| Sugar g/L | 15-45 | 22-37 | 27-33 | 30 | 30 ± 2 |
| Agar g/L | 2.7-8.2 | 4.1-6.8 | 4.9-6.1 | 5.5 | 5.5 ± 0.2 |

Media BR-2(i-v):

| Component | BR-2-i | BR-2-ii | BR-2-iii | BR-2-iv | BR-2-v |
|---|---|---|---|---|---|
| $NH_4NO_3$ | 700-2100 | 1050-1750 | 1260-1540 | 1400 | 1400 ± 2 |
| $Ca(NO_3)_2$ | 973-2919 | 1459-2433 | 1752-2140 | 1946 | 1946 ± 2 |
| $K_2SO_4$ | 606.3-1818.8 | 909.4-1515.6 | 1091.5-1333.5 | 1212.5 | 1212.5 ± 0.2 |
| $MgSO_4$ | 370-1110 | 555-925 | 665-815 | 740 | 740 ± 2 |
| $MnSO_4$ | 16.9-50.7 | 25.4-42.3 | 30.5-37.1 | 33.8 | 33.8 ± 0.2 |
| $ZnSO_4$ | 8.6-25.8 | 12.9-21.5 | 15.5-18.0 | 17.2 | 17.2 ± 0.2 |
| $CuSO_4$ | 0.02-0.08 | 0.03-0.07 | 0.04-0.06 | 0.05 | 0.05 ± .02 |
| $CaCl_2$ | 72-216 | 108-180 | 130-158 | 144 | 144 ± 2 |
| $H_3BO_3$ | 3.0-9.0 | 4.0-8.0 | 5.0-7.0 | 6.2 | 6.2 ± 0.2 |
| $Na_2MoO_4$ | 0.12-0.36 | 0.18-0.31 | .22-.28 | 0.25 | 0.25 ± .02 |
| $KH_2PO_4$ | 72-342 | 202-338 | 243-297 | 270 | 270 ± 2 |
| $FeSO_4$ | 16.68-50.04 | 25.02-41.70 | 30.06-36.66 | 33.36 | 33.36 ± .02 |
| $Na_2EDTA$ | 22.38-67.14 | 33.57-55.95 | 40.36-49.16 | 44.76 | 44.76 ± .02 |
| myo-Inositol | 100-300 | 150-250 | 180-220 | 200 | 200 ± 2 |
| Thiamine | 0.4-1.4 | 0.6-1.2 | 0.8-1.0 | 0.9 | 0.9 ± 0.2 |
| Pyridoxine | 0.2-0.8 | 0.3-0.7 | 0.4-0.6 | 0.5 | 0.5 ± 0.2 |
| Nicotinic acid | 0.2-0.8 | 0.3-0.7 | 0.4-0.6 | 0.5 | 0.5 ± 0.2 |
| Glycine | 1-3 | 1.5-2.5 | 1.75-2.25 | 2 | 2 ± 1 |
| Riboflavin | 10-30 | 15-25 | 18-22 | 20 | 20 ± 2 |
| Ascorbic Acid | 50-150 | 75-125 | 90-110 | 100 | 100 ± 2 |
| NAA | 0.2-0.8 | 0.3-0.7 | 0.4-0.6 | 0.5 | 0.5 ± 0.2 |
| Sugar g/L | 15-45 | 22-37 | 27-33 | 30 | 30 ± 2 |
| Carrageenan g/L | 4-12 | 6-10 | 7-9 | 8 | 8 ± 2 |
| Charcoal g/L | 150-450 | 220-370 | 270-330 | 300 | 300 ± 2 |

Media Amel(i-v):

| Component | Amel-i | Amel-ii | Amel-iii | Amel-iv | Amel-v |
|---|---|---|---|---|---|
| $NH_4NO_3$ | 410-1240 | 620-1030 | 740-910 | 825 | 825 ± 2 |
| $Ca(NO_3)_2$ | 475-1425 | 710-1190 | 855-1045 | 950 | 950 ± 2 |
| $MgSO_4$ | 90-280 | 140-230 | 160-200 | 185 | 185 ± 2 |
| $MnSO_4$ | 4.20-12.70 | 6.30-10.60 | 7.65-9.25 | 8.45 | 8.45 ± .02 |
| $ZnSO_4$ | 2.0-6.5 | 3.0-5.5 | 3.5-5.0 | 4.3 | 4.3 ± 0.2 |
| $CuSO_4$ | .0062-.0188 | .0094-.0156 | .0115-.0135 | 0.0125 | 0.0125 ± .0002 |
| $CaCl_2$ | 110-330 | 165-285 | 195-240 | 220 | 220 ± 2 |
| KI | .207-.623 | .310-.520 | .375-.455 | 0.415 | 0.415 ± .002 |
| $H_3BO_3$ | 1.5-4.6 | 2.3-4.0 | 2.8-3.4 | 3.1 | 3.1 ± 0.2 |
| $CaCl_2$ | .0062-.0188 | .0094-.0156 | .0115-.0135 | 0.0125 | 0.0125 ± .0002 |
| $Na_2MoO_4$ | .062-.188 | .093-.157 | .115-.135 | 0.125 | 0.125 ± .002 |
| $KH_2PO_4$ | 40-130 | 60-110 | 75-95 | 85 | 85 ± 2 |
| $FeSO_4$ | 6.8-20.9 | 10.4-17.5 | 12.5-15.5 | 13.9 | 13.9 ± 0.2 |
| $Na_2EDTA$ | 9.32-27.98 | 13.95-23.35 | 16.85-20.45 | 18.65 | 18.65 ± .02 |
| $Na_2H_2PO_4$ | 40-130 | 60-110 | 75-95 | 85 | 85 ± 2 |
| myo-Inositol | 50-150 | 75-125 | 90-110 | 100 | 100 ± 2 |
| Thiamine | 0.2-0.6 | 0.3-0.5 | 0.36-0.44 | 0.4 | 0.4 ± .2 |
| Pyridoxine | 0.2-0.8 | 0.3-0.7 | 0.4-0.6 | 0.5 | 0.5 ± 0.2 |
| Nicotinic acid | 1-3 | 1.5-2.5 | 1.75-2.25 | 2 | 2 ± 1 |
| Riboflavin | 2.5-7.5 | 3.7-6.2 | 4.5-5.5 | 5 | 5 ± 2 |
| NAA | 0.2-0.8 | 0.3-0.7 | 0.4-0.6 | 0.5 | 0.5 ± 0.2 |
| IBA | 0.5-1.5 | 0.7-1.3 | 0.9-1.1 | 1 | 1 ± 0.5 |
| Sugar g/L | 15-45 | 22-37 | 27-33 | 30 | 30 ± 2 |
| Agar g/L | 1.5-4.5 | 2.0-4.0 | 2.5-3.5 | 3 | 3 ± 2 |
| Carrageenan g/L | 2.5-7.5 | 3.7-6.2 | 4.5-5.5 | 5 | 5 ± 2 |
| Charcoal g/L | 2.5-7.5 | 3.7-6.2 | 4.5-5.5 | 5 | 5 ± 2 |

During transition to ex vitro conditions, shoots and media can be placed in air permeable or air impermeable containers.

Each of the media described herein can be used in combination with each other media in a method, system or kit described herein. Moreover, the media can be combined in combinations greater than two (e.g., a kit may include 2 of the different media provided herein, or include 3 of the different media provided herein, or include more than 3 of the different media described herein). While not explicitly describing each possible combination herein, one of ordinary skill in the art should understand that this disclosure supports all possible combinations.

Following transition to ex vitro conditions, but before plants are placed in soil, or exposed to less regulated growing conditions, the plants can undergo a series of treatments designed to acclimate them to an unregulated growing environment. This is because some plants, when microcultured, do not develop adequate defensive structures, such as waxy cuticles to protect them from ordinary environmental conditions. The treatments that plants can undergo prior to being placed in an unregulated environment can include, without limitation, acclimatization to humidity, acclimatization to variations in temperature, and acclimatization to wind pressure. These acclimatization factors can be introduced gradually and/or in a staggered fashion.

Representative genus of bamboo appropriate for use with the disclosures herein include: *Acidosasa; Ampelocalamus; Arundinaria; Bambusa; Bashania; Borinda; Brachystachyum; Cephalostachyum; Chimonobambusa; Chimonocalamus; Chusquea; Dendrocalamus; Dinochloa; Drepanostachyum; Eremitis; Fargesia; Gaoligongshania; Gigantochloa; Guadua; Hibanobambusa; Himalayacalamus; Indocalamus; Indosasa; Lithachne; Melocalamus; Melocanna; Menstruocalamus; Nastus; Neohouzeaua; Neololeba; Ochlandra; Oligostachyum; Olmeca; Otatea; Oxytenanthera; Phyllostachys; Pleioblastus; Pseudosasa; Raddia; Rhipidocladum; Sarocalamus; Sasa; Sasaella; Sasamorpha; Schizostachyum; Semiarundinaria; Shibataea; Sinobambusa; Thamnocalamus; Thyrsostachys;* and *Yushania*.

Non-limiting examples of species within these genus include:

Acidosasa: Edulis

Ampelocalamus: Scandens

Arundinaria: *Arundinaria appalachiana; Arundinaria funghomii; Arundinaria gigantea; Arundinaria gigantea* 'Macon'; and *Arundinaria Tecta*

Bambusa: *arnhemica; balcooa; bambos; basihirsuta; beecheyana; beecheyana* var *pubescens; blumeana; boniopsis; burmanica; chungii; chungii* var. *Barbelatta; cornigera; dissimulator, dissimulator* 'Albinodia'; *distegia; dolichoclada; dolichoclada* 'Stripe'; *dolichomerithalla* 'Green stripe'; *dolichomerithalla* 'Silverstripe'; *emeiensis* 'Chrysotrichus'; *emeiensis* 'Flavidovirens'; *emeiensis* 'Viridiflavus'; *eutuldoides; eutuldoides* 'Viridivittata'; *gibba; glaucophylla; intermedia; lako; lapidea; longispiculata; maculata; malingensis; multiplex; multiplex* 'Alphonse Karr'; *multiplex* 'Fernleaf Stripestem'; *multiplex* 'Fernleaf'; *multiplex* 'Golden Goddess'; *multiplex* 'Goldstripe'; *multiplex* 'Midori Green'; *multiplex* 'Riviereorum'; *multiplex* 'Silverstripe'; *multiplex* 'Tiny Fern Striped'; *multiplex* 'Tiny Fern'; *multiplex* 'Willowy'; *nutans; odashimae; odashimae×B. Tuldoides; oldhamii; oliveriana; pachinensis; pervariabilis; pervariabilis* 'Viridistriatus'; *rigida; rutila; sinospinosa*; sp 'Hirose'; sp. 'Clone X'; sp. 'Nana'; sp. 'Polymorpha'; sp. 'Richard Waldron'; *stenostachya; suberecta; textilis; textilis* 'Dwarf'; *textilis* 'Kanapaha'; *textilis* 'Maculata'; *textilis* 'Mutabilis'; *textilis* 'Scranton'; *textilis* var. *Albostriata; textilis* var. *Glabra; textilis* var. *Gracilis; tulda; tulda* 'Striata'; *Tuldoides; variostriata; ventricosa; ventricosa* 'Kimmei'; *vulgaris; vulgaris* 'Vittata'; *vulgaris* 'Wamin Striata'; and *vulgaris* 'Wamin'

Bashania: *Fargesii*; and *Qingchengshanensis*

Borinda: KR 5288; *Albocerea; Angustissima; Contracta; Frigidorum; Fungosa; fungosa* 'White Cloud'; *Lushuiensis; Macclureana; Nujiangensis; Papyrifera; Perlonga*; sp. 'Muliensis'; and *Yulongshanensis*

Brachystachyum: *densiflorum*; and *densiflorum* var. *villosum*

*Cephalostachyum: Pergracile*; and *Virgatum*

*Chimonobambusa: macrophylla* 'Intermedia'; *Marmorea; marmorea* 'Variegata'; *Quadrangularis; quadrangularis* 'Joseph de Jussieu'; *quadrangularis* 'Suow'; *quadrangularis* 'Yellow Groove'; *Szechuanensis*; and *Tumidissinoda*

*Chimonocalamus: Pallens*

*Chusquea: Andina; Circinata; circinata* 'Chiapas' *Coronalis; Culeou; culeou* 'Argentina'; *culeou* 'Caña Prieta'; *culeou* 'Hillier's Form'; *Cumingii; Delicatula; Foliosa; Galeottiana; Gigantea; Glauca; Liebmannii; Macrostachya; mimosa* ssp. *Australis; Montana; Muelleri; Pittieri; Simpliciflora*; sp. 'Chiconquiaco'; sp. 'Las Vigas'; *Subtilis; Sulcata; Tomentosa; Uliginosa; Valdiviensis*; and *Virgata*

*Dendrocalamus: Asper, asper* 'Betung Hitam'; *Brandisii; brandisii* 'Black'; *brandisii* (variegated); *Calostachyus; Giganteus; giganteus* (Quail Clone); *giganteus* (variegated); *Hamiltonii; Jianshuiensis; jianshuiensis* (variegated); *Latiflorus; latiflorus* 'Mei-nung'; *Membranaceus; Minor; minor* 'Amoenus'; *Sikkimensis; Sinicus*; sp. 'Maroochy'; sp. 'Parker's Giant'; *Strictus; Validus*; and *Yunnanicus*

*Dinochloa: Malayana*; and *Scandens*

*Drepanostachyum: falcatum* var. *sengteeanum*; and *Khasianum*

*Eremitis: Eremitis*

*Fargesia: Adpressa; Apircirubens; apircirubens* 'White Dragon'; *Denudata; dracocephala* 'Rufa'; *Murieliae; murieliae* 'SABE 939'; *murieliae* 'Vampire'; *murieliae* (next generation seedlings); *Nitida; nitida* 'Jiuzhaigou'; *Robusta; robusta* 'Campbell'; *robusta* 'Wolong'; sp. 'Scabrida'; and *Utilis*

*Gaoligongshania: Gaoligongshania* and *Megalothyrsa*

*Gigantochloa: Hitam Hijau; Albociliata; Apus; Atroviolacea; Atter; Hasskarliana; Levis; Luteostriata; Maxima; Pseudoarundinacea; Ridleyi; Robusta*; sp 'Rachel Carson'; sp. 'Bali White Stripe'; sp. 'Sumatra 3751'; sp. 'Widjaja 3827'; and *Wrayii*

*Guadua: Amplexifolia; Angustifolia; angustifolia* 'Bicolor'; *angustifolia* 'Less Thorny'; *Chacoensis; Longifolia; Paniculata*; sp. 'Aureocaulis'; and *Velutina*

*Hibanobambusa: Tranquillans*; and *tranquillans* 'Shiroshima'

*Himalayacalamus: Falconeri; falconeri* 'Damarapa'; *Hookerianus; Planatus*; and *Porcatus*

*Indocalamus: Cordatus; Latifolius; latifolius* 'Hopei'; *Longiauritus*; sp. 'Hamadae'; sp. 'Solidus'; *Tessellatus*; and *Victorialis*

*Indosasa: Crassiflora*; and *Gigantea*

*Lithachne: Humilis*

*Melocalamus: Arrectus*

*Melocanna: Baccifera*

*Menstruocalamus: Sichuanensis*

*Nastus: Elatus*

*Neohouzeaua: Mekongensis*

*Neololeba: Atra*

*Ochlandra: Stridula*

*Oligostachyum: Glabrescens*

*Olmeca: Recta*

*Otatea: acuminata* 'Michoacan'; *acuminata* ssp. *Acuminata; acuminata* ssp. *Aztecorum; acuminata* ssp. *aztecorum* 'Dwarf'; *Fimbriata*; and *glauca* 'Mayan Silver'

*Oxytenanthera: Abyssinica*; and *Braunii*

*Phyllostachys: Acuta; Angusta; Arcana; arcana* 'Luteosulcata'; *Atrovaginata; Aurea; aurea* 'Albovariegata'; *aurea* 'Dr Don'; *aurea* 'Flavescens-inversa'; *aurea* 'Holochrysa'; *aurea* 'Koi'; *aurea* 'Takemurai'; *Aureosulcata; aureosulcata* 'Alata'; *aureosulcata* 'Aureocaulis'; *aureosulcata* 'Harbin Inversa'; *aureosulcata* 'Harbin'; *aureosulcata* 'Pekinensis'; *aureosulcata* 'Spectabilis'; *Aurita; Bambusoides; bambusoides* 'Albovariegata'; *bambusoides* 'Castillon Inversa'; *bambusoides* 'Castillon'; *bambusoides* 'Golden Dwarf'; *bambusoides* 'Job's Spot'; *bambusoides* 'Kawadana'; *bambusoides* 'Marliac'; *bambusoides* 'Rib Leaf'; *bambusoides* 'Richard Haubrich'; *bambusoides* 'Slender Crookstem'; *bambusoides* 'Subvariegata'; *bambusoides* 'Tanakae'; *bambusoides* 'White Crookstem'; *Bissetii; bissetii* 'Dwarf'; *Dulcis; Edulis; edulis* 'Anderson'; *edulis* 'Bicolor'; *edulis* 'Goldstripe'; *edulis* 'Heterocycla'; *Elegans; Flexuosa; flexuosa* 'Kimmei'; *Glauca; glauca* 'Notso'; *glauca* 'Yunzhu'; *Heteroclada; heteroclada* 'Purpurata'; *heteroclada* 'Solidstem'; *Hispida; Humilis; Incarnata; Iridescens; Kwangsiensis; Lithophila; Lofushanensis; Makinoi; mannii* 'Decora'; *mannii* 'Mannii'; *Meyeri; Nidularia; nidularia* 'Farcta'; *nidularia* 'Smoothsheath'; *Nigra; nigra* 'gory'; *nigra* 'Daikokuchiku'; *nigra* 'Hale'; *nigra* 'Henon'; *nigra* 'Megurochiku'; *nigra* 'Mejiro'; *nigra* 'Muchisasa'; *nigra* 'Othello'; *nigra* 'Punctata'; *nigra* 'Shimadake'; *nigra* 'Tosaensis'; *Nuda; nuda* 'Localis'; *Parvifolia; Platyglossa; Praecox; praecox* 'Prevernalis'; *praecox* 'Viridisulcata'; *Prominens; Propinqua; propinqua* 'Beijing'; *Robustiramea; Rubromarginata; Stimulosa; Varioauriculata; Violascens; Viridiglaucescens; Viridis; viridis* 'Houzeau'; *viridis* 'Robert Young'; *Vivax; vivax* 'Aureocaulis'; *vivax* 'Black Spot'; *vivax* 'Huangwenzhu Inversa'; and *vivax* 'Huangwenzhu'

*Pleioblastus: Akebono; Amarus; Argenteostriatus; Chino; chino* 'Angustifolia'; *chino* 'Elegantissimus'; *chino* 'Kimmei'; *chino* 'Murakamiansus'; *chino* 'Vaginatus Variegatus'; *Distichus; distichus* 'Mini'; *Fortunei; Gauntlettii; Gramineus; gramineus* 'Monstrispiralis'; *Hindsii; Humilis; humilis* 'Albovariegatus'; *humilis* 'Variegatus'; *Juxianensis; Kodzumae; Kongosanensis; kongosanensis* 'Akibensis'; *kongosanensis* 'Aureostriatus'; *Linearis; linearis* 'Nana'; *Nagashima; Oleosus; Pygmaeus; pygmaeus* 'Greenstripe'; *pygmaeus* 'Ramosissimus'; *shibuyanus* 'Tsuboi'; *Simonii; simonii* 'Variegatus'; *Viridistriatus; viridistriatus* 'Chrysophyllus'; and *Xestrophyllus*

*Pseudosasa: Amabilis; Cantori; Guanxianensis; Japonica; japonica* 'Akebono'; *japonica* 'Akebono-suji'; *japonica* 'Pleioblastoides'; *japonica* 'Tsutsumiana'; *japonica* 'Variegata'; *Longiligula; Owatarii; Usawai*; and *Viridula*

*Raddia: Brasiliensis*; and *Distichophylla*

*Rhipidocladum: Pittieri*; and *Racemiflorum*

*Sarocalamus: Faberi*; and *Fangianus*

*Sasa: Cernua; Gracillima; Hayatae; Kagamiana; kagamiana* ssp. *Yoshinoi; Kurilensis; kurilensis* 'Shimofuri'; *Megalophylla; Nagimontana; nipponica* (hort.); *Oshidensis; Palmata; Senanensis; Shimidzuana*; sp. *Tsuboiana*; and *Veitchii*

*Sasaella: Bitchuensis; hidaensis* 'muraii'; *Masamuneana; masamuneana* 'Albostriata'; *masamuneana* 'Aureostriata'; *Ramosa; Sasakiana*; and *Shiobarensis*

*Sasamorpha: Borealis*

*Schizostachyum: Brachycladum; brachycladum* 'Bali Kuning'; *Caudatum; Glaucifolium; Jaculans; Lima*; and sp. 'Murray Island'

*Semiarundinaria: Fastuosa; fastuosa* 'Viridis'; *Fortis; Kagamiana; Lubrica; Makinoi; Okuboi*; sp. Maruyamana; sp. 'Korea'; *Yashadake; yashadake* 'Kimmei'; and *yashadake* 'kimmei inversa'

*Shibataea: Chinensis; Kumasaca; kumasaca* 'Albostriata'; *kumasaca* 'Aureostriata'; *Lancifolia*; and *Nanpingensis*

*Sinobambusa: Gigantea; Intermedia; Tootsik*; and *tootsik* 'Albostriata'

*Thamnocalamus: aristatus* 'Aristatus hort. US'; *Crassinodus; crassinodus* 'Kew Beauty'; *crassinodus* 'Mendocino'; *crassinodus* 'Merlyn'; *nepalensis* 'Nyalam'; *Spathiflorus*; and *Tessellatus*

*Thyrsostachys: Oliveri*; and *Siamensis*

*Yushania: Alpina; Anceps; anceps* 'Pitt White'; *Boliana; Brevipaniculata; Exilis; Maculata*; and *maling*

Particularly useful species include: *edulis; scandens; Arundinaria Gigantea; Arundinaria Tecta; Bambusa Balcooa; Bambusa Bambos; Bambusa Oldhamii; Bambusa Textilis; Bambusa Tulda; Bashania Fargesii; Brachystachyum Densiflorum; Chusquea Gigantea; Dendrocalamus Asper; Dendrocalamus Brandisii; Dendrocalamus Giganteus; Dendrocalamus Hamiltonii; Dendrocalamus Strictus; Fargesia Denudata; Fargesia dracocephala*'Rufa'; *Fargesia Murieliae; Fargesia Nitida; Fargesia Robusta; Fargesia robusta* 'Wolong'; *Fargesia* sp. 'Scabrida'; *Guadua Amplexifolia; Guadua Paniculata; Himalayacalamus Falconeri; Indocalamus Tessellatus; Ochlandra Stridula; Otatea acuminata* ssp. *Aztecorum; Phyllostachys Atrovaginata; Phyllostachys Aurea; Phyllostachys Bambusoides; Phyllostachys Bissetii; Phyllostachys Edulis; Phyllostachys edulis* 'Heterocycla'; *Phyllostachys Glauca; Phyllostachys Iridescens; Phyllostachys Kwangsiensis; Phyllostachys Nidularia; Phyllostachys Nigra; Phyllostachys nigra* 'Henon'; *Phyllostachys Nuda; Phyllostachys Parvifolia; Phyllostachys Praecox; Phyllostachys Propinqua; Phyllostachys Viridis; Phyllostachys Vivax; Pleioblastus Distichus; Pleioblastus Fortunei; Pleioblastus Linearis; Pseudosasa Japonica; Sasa Kurilensis; Sasa Veitchii; Sasaella Masamuneana; Sasamorpha Borealis; Schizostachyum Brachycladum; Schizostachyum brachycladum* 'Bali Kuning'; *Schizostachyum Caudatum; Schizostachyum Glaucifolium; Schizostachyum Jaculans; Schizostachyum Lima; Schizostachyum* sp. 'Murray Island'; *Semiarundinaria Fastuosa; Semiarundinaria Yashadake; Shibataea Kumasaca; Sinobambusa Gigantea; Thamnocalamus Crassinodus; Thamnocalamus Tessellatus; Yushania Alpina*; and *Yushania maling*.

As one of ordinary skill in the art appreciates, many species of bamboo have different common names. Accordingly, the following terminology and language comparisons are provided.

| Classic Name | Equivalent |
|---|---|
| ACIDOSASA gigantea | INDOSASA gigantea |
| ARTHROSTYLIDIUN sp. (hort) | CHUSQUEA circinata |
| ARUNDINARIA alpina | YUSHANIA alpina |
| ARUNDINARIA amabilis | PSEUDOSASA amabilis |
| ARUNDINARIA anceps | YUSHANIA anceps |
| ARUNDINARIA auricoma | PLEIOBLASTUS viridistriatus |
| ARUNDINARIA falconeri | DREPANOSTACHYUM falcatum 'var. sengteeanum' |
| ARUNDINARIA fangiana | SAROCALAMUS fangianus |
| ARUNDINARIA hookerianus | HIMALAYACALAMUS hookerianus |
| ARUNDINARIA macrosperma | ARUNDINARIA gigantea |
| ARUNDINARIA maling | YUSHANIA maling |
| ARUNDINARIA tessellata | THAMNOCALAMUS tessellatus |
| ARUNDINARIA vagans | SASAELLA ramosa |
| BAMBUSA arundinacea | BAMBUSA bambos |
| BAMBUSA dissemulator | BAMBUSA dissimulator |
| BAMBUSA edulis | BAMBUSA odashimae |
| BAMBUSA forbesii | NEOLOLEBA atra |
| BAMBUSA glaucescens | BAMBUSA multiplex |
| BAMBUSA multiplex 'Green Alphonse' | BAMBUSA multiplex 'Midori Green' |
| Bambusa mutabilis | Bambusa textilis 'Mutabilis' |
| Bambusa tuldoides 'Clone X' | Bambusa sp. 'Clone X' |
| Bambusa tuldoides 'ventricosa' | Bambusa ventricosa |
| Bambusa variegata (hort.) | Bambusa glaucophylla |
| BAMBUSA vulgaris 'Striata' | BAMBUSA vulgaris 'Vittata' |
| BASHANIA faberi | SAROCALAMUS faberi |
| Borinda boliana | Yushania boliana |
| CHIMONOBAMBUSA falcata | HIMALYACALAMUS hookerianus |
| CHUSQUEA breviglumis | CHUSQUEA gigantea |
| Chusquea breviglumis | Chusquea culeou |
| CHUSQUEA nigricans | CHUSQUEA culeou 'Ca?a Prieta' |
| CHUSQUEA quila | CHUSQUEA valdiviensis |
| DENDROCALAMUS affinis | BAMBUSA emeiensis |
| DENDROCALAMUS membranaceus | BAMBUSA membranacea |
| DREPANOSTACHYUM falcatum | HIMALAYACALAMUS hookerianus |
| DREPANOSTACHYUM falconeri | DREPANOSTACHYUM falcatum 'var. sengteeanum' |
| DREPANOSTACHYUM hookerianum | HIMALAYACALAMUS falconeri 'Damarapa' |
| DREPANOSTACHYUM sengteeanum | HIMALAYACALAMUS falconeri |
| FARGESIA angustissima | BORINDA angustissima |
| FARGESIA crassinodus | THAMNOCALAMUS crassinodus |
| Fargesia dracocephala | Fargesia apircirubens |
| Fargesia dracocephala 'White Dragon' | Fargesia apircirubens 'White Dragon' |
| FARGESIA frigida | BORINDA frigidorum |
| FARGESIA fungosa | BORINDA fungosa |
| FARGESIA sp "A-4" | FARGESIA adpressa |
| Fargesia sp. 'rufa' | Fargesia dracocephala 'Rufa' |
| GELIDOCALAMUS fangianus | SAROCALAMUS fangianus |
| GIGANTOCHLOA atroviolacea 'Timor Black' | BAMBUSA lako |

| Classic Name | Equivalent |
| --- | --- |
| *GIGANTOCHLOA luteostriata* | *BAMBUSA luteostriata* |
| *GIGANTOCHLOA verticillata* | *GIGANTOCHLOA pseudoarundinacea* |
| *Himalayacalamus asper* | *Himalayacalamus planatus* |
| *HIMALAYACALAMUS falconeri* 'glomeratum' | *DREPANOSTACHYUM falcatum* 'var. sengteeanum' |
| *HIMALAYACALAMUS intermedius* | *Yushania boliana* |
| *HIMALAYACALAMUS planatus* | *HIMALAYACALAMUS asper* (hort.) |
| *HIMALAYACALAMUS planatus* | *Neomicrocalamus microphyllus* (hort.) |
| *NEOMICROCALAMUS microphyllus* | *HIMALAYACALAMUS planatus* |
| *NEOSINOCALAMUS affinis* | *BAMBUSA emeiensis* 'Chrysotrichus' |
| *Otatea acuminata* 'Mayan Silver' | *Otatea glauca* 'Mayan Silver' |
| *OTATEA aztecorum* | *OTATEA acuminata* ssp. *aztecorum* |
| *PHYLLOSTACHYS cerata* | *PHYLLOSTACHYS heteroclada* |
| *PHYLLOSTACHYS congesta* | *PHYLLOSTACHYS atrovaginata* |
| *PHYLLOSTACHYS decora* | *PHYLLOSTACHYS mannii* 'Decora' |
| *PHYLLOSTACHYS heterocycla* | *PHYLLOSTACHYS edulis* 'Heterocycla' |
| *PHYLLOSTACHYS heterocycla pubescens* | *PHYLLOSTACHYS edulis* |
| *PHYLLOSTACHYS heterocycla pubescens* 'Anderson' | *PHYLLOSTACHYS edulis* 'Anderson' |
| *PHYLLOSTACHYS purpurata* | *PHYLLOSTACHYS heteroclada* 'Purpurata' |
| *PHYLLOSTACHYS purpurata* 'Solidstem' | *PHYLLOSTACHYS heteroclada* 'Solidstem' |
| *PHYLLOSTACHYS purpurata* 'Straightstem' | *PHYLLOSTACHYS heteroclada* |
| *PLEIOBLASTUS akibensis* | *PLEIOBLASTUS kongosanensis* 'Akibensis' |
| *PLEIOBLASTUS gramineus* 'Raseetsuchiku' | *PLEIOBLASTUS gramineus* 'Monstrispiralis' |
| *PLEIOBLASTUS variegatus* | *PLEIOBLASTUS fortunei* |
| *Qiongzhuea tumidissinoda* | *Chimonobambusa tumidissinoda* |
| *SASA asahinae* | *SASA shimidzuana* |
| *SASA humilis* | *PLEIOBLASTUS humilis* |
| *SASA pygmaea* | *PLEIOBLASTUS pygmaeus* |
| *SASA tessellata* | *INDOCALAMUS tessellatus* |
| *SASA variegata* | *PLEIOBLASTUS fortunei* |
| *Sasa veitchii* 'Minor' | *Sasa hayatae* |
| *SASAELLA glabra* 'Albostriata' | *SASAELLA masamuneana* 'Albostriata' |
| *SASAELLA masamuneana rhyncantha* | *SASAELLA masamuneana* |
| *SASAELLA rhyncantha* | *SASAELLA masamuneana* |
| *SEMIARUNDINARIA villosa* | *SEMIARUNDINARIA okuboi* |
| *SINARUNDINARIA* | *FARGESIA* |
| *TETRAGONOCALAMUS angulatus* | *CHIMONOBAMBUSA quadranqularis* |
| *THAMNOCALAMUS spathaceus* | *FARGESIA murieliae* |
| *YUSHANIA aztecorum* | *OTATEA acuminata* ssp. *aztecorum* |

Chinese & Japanese Names

| Chinese | Botanical | Japanese | Botanical |
| --- | --- | --- | --- |
| Cha Gang zhu | *Pseudosasa amabilis* | Hachiku | *Phyllostachys nigra* 'Henon' |
| Che Tong zhu | *Bambusa sinospinosa* | Hoteichiku | *Phyllostachys aurea* |
| Fang zhu | *Chimonobambusa quadrangularis* | Kikkochiku | *Phyllostachys edulis* 'Heterocycla' |
| Fo du zhu | *Bambusa ventricose* | Kumazasa | *Sasa veitchii* (not *Shibataea kumasaca*) |
| Gui zhu | *Phyllostachys bambusoides* | Kurochiku | *Phyllostachys nigra* |
| Han zhu | *Chimonobambusa marmorea* | Madake | *Phyllostachys bambusoides* |
| Hong Bian zhu | *Phyllostachys rubromarginata* | Medake | *Pleioblastus simonii* |
| Hou zhu | *Phyllostachys nidularia* | Moso | *Phyllostachys edulis* |
| Hui Xiang zhu | *Chimonocalamus pallens* | Narihira | *Semiarundinaria fastuosa* |
| Jin zhu | *Phyllostachys sulphurea* | Okame-zasa | *Shibataea kumasaca* |
| Ma zhu | *Dendrocalamus latiflorus* | Yadake | *Pseudosasa japonica* |
| Mao zhu | *Phyllostachys edulis* | | |
| Qiong zhu | *Chimonobambusa tumidissinoda* | | |
| Ren Mian zhu | *Phyllostachys aurea* | | |
| Shui zhu | *Phyllostachys heteroclada* | | |
| Wu Ya zhu | *Phyllostachys atrovaginata* | | |
| Xiang Nuo zhu | *Cephalostachyum pergracile* | | |
| Zi zhu | *Phyllostachys nigra* | | |

English Names

| English | Botanical | English | Botanical |
| --- | --- | --- | --- |
| Arrow | *Pseudosasa japonica* | "Lucky Bamboo" | *Dracaena sanderiana*[1] |

-continued

| English | Botanical | English | Botanical |
|---|---|---|---|
| Beechey | Bambusa beecheyana | Male | Dendrocalamus strictus |
| Blue | Himalayacalamus hookerianus | Marbled | Chimonobambusa marmorea |
| Black | Phyllostachys nigra | Mexican Weeping | Otatea acuminate subsp. aztecorum |
| Buddha's Belly | Bambusa ventricose | Monastery | Thyrsostachys siamensis |
| Candy Stripe or Candy cane | Himalayacalamus falconeri 'Damarapa' | Oldham's | Bambusa oldhamii |
| Canebrake | Arundinaria gigantea | Painted | Bambusa vulgaris 'Vittata' |
| Chinese Goddess | Bambusa multiplex 'Riviereorum' | Punting Pole | Bambusa tuldoides |
| Chinese Thorny | Bambusa sinospinosa | River Cane | Arundinaria gigantea |
| Common | Bambusa vulgaris | Square | Chimonobambusa quadrangularis |
| Dwarf Fern Leaf | Pleioblastus distichus | Stone | Phyllostachys angusta & P. nuda |
| Dwarf Whitestripe | Pleioblastus fortunei | Sweetshoot | Phyllostachys dulcis |
| Fernleaf | Bambusa multiplex 'Fernleaf' | Switch Cane | Arundinaria tecta |
| Fountain | Fargesia nitida | Tea Stick | Pseudosasa amabilis |
| Giant Thorny | Bambusa bambos | Temple | Semiarundinaria fastuosa |
| Giant Timber | Bambusa oldhamii | Timor Black | Bambusa lako |
| Green Mountain | Yushania alpina | Tonkin Cane | Pseudosasa amabilis |
| Golden | Phyllostachys aurea | Tortoise Shell | Phyllostachys edulis 'Heterocycla' |
| Golden Golden | Phyllostachys aurea 'Holochrysa' | Tropical Black | Gigantochloa atroviolacea |
| "Heavenly Bamboo" | not a bamboo (Nandina domestica) | Umbrella | Fargesia murieliae |
| Hedge | Bambusa multiplex | Water | Phyllostachys heteroclada |
| Himalayan Blue | Himalayacalamus hookerianus | Weaver's | Bambusa textilis |
| Horsehoof | Bambusa lapidea | Wine | Oxytenanthera braunii |
| Iron Range | Neololeba atra | Yellow Groove | Phyllostachys aureosulcata |
| Japanese Timber | Phyllostachys bambusoides | | |

[1]Technically not a bamboo but included within the meaning of bamboo herein.

By means of the media, systems and methods described and disclosed herein, it is possible for one of ordinary skill in the art to achieve rolling tissue cultures of bamboo. As used herein, "rolling tissue culture" means that the multiplication process can continue substantially indefinitely by continuing to separate and multiply shoots. In one embodiment, one shoot is placed in a tube and the shoot multiplies into a number of additional shoots. After multiplication, each shoot or a subset of the shoots are separated and each placed in a subsequent tube for further multiplication. This process can continue while at various times, some or all shoots can be removed from the multiplication process and transitioned to ex vitro conditions. By continuing indefinitely, it is meant that 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, etc. day multiplication cycles can be repeated without initiating new explants for at least 1 month, for at least 3 months, for at least 6 months, for at least 9 months, for at least 12 months, for at least 15 months, for at least 18 months, for at least 21 months, for at least 24 months or for at least 36 months. Particular ranges of days in multiplication cycles include 10-120 days; 10-100 days; 10-80 days; 10-60 days; 10-42 days; 10-40 days; 10-20 days; 14-120 days; 14-90 days; 14-70 days; 14-50; 14-42 days; 14-30 days; 14-21 days; 12-42 days; 20-60 days; 10-15 days; 14-20 days; 14-18 days etc.

These media systems and methods can be packaged and/or described in various kits. Kits can include, without limitation, one or more of the following in a package or container: (1) one or more media; and (2) one or more explants from one or more species of bamboo. In certain non-limiting embodiments, the media can be b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media, CW6-v media, Br-2-i media, Br-2-ii media, Br-2-iii media, Br-2-iv media, Ech-i media, Ech-ii media, Ech-iii media, Ech-iv, Amel-i media, Amel-ii media, Amel-iii media, Amel-iv media or Amel-v. In another embodiment, the kits can comprise one or more containers for the tissue culturing process including without limitation, tubes, jars, boxes or jugs. In another embodiment the kits can comprise instructions for the tissue culturing of bamboo. In another embodiment, the kits comprise combinations of the foregoing. Components of various kits can be found in the same or different containers. Additionally, when a kit is supplied, the different components of the media can be packaged in separate containers and admixed immediately before use. Such packaging of the components separately may permit long-term storage without losing the active components' functions. Alternatively, media can be provided pre-mixed.

The ingredients included in the kits can be supplied in containers of any sort such that the life of the different ingredients are preserved and are not adsorbed or altered by the materials of the container. For example, sealed glass ampules may contain ingredients that have been packaged under a neutral, non-reacting gas, such as nitrogen. Ampules may consist of any suitable material, such as glass, organic polymers, such as polycarbonate, polystyrene, etc., ceramic, metal or any other material typically employed to hold similar ingredients. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced. Other containers may have two compartments that are separated by a readily removable membrane that upon removal permits the ingredients to be mixed. Removable membranes may be glass, plastic, rubber, etc.

As stated, kits can be supplied with instructional materials. Instructions may be printed on paper or other substrate, and/or may be supplied as an electronic-readable media, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

One advantage of the disclosed embodiments is that the methods are more robust than those previously used producing plants that do not require special treatments required by those produced using methods of the prior art. For example, methods disclosed herein do not require the use of seeds or inflorescence to start plants; do not require selection of diseased starting plants (such as those exhibiting symptoms of witches broom or little leaf disease); do not require use of somatic embryogenesis and do not utilize pseudospiklets. For successful growth following tissue culture, the produced plants do not require watering directly on the pot but remain robust with overhead watering and do not require multiple adjustments to light intensity or humidity conditions prior to transfer to a greenhouse or other growing conditions. These improvements over prior methods provide even additional advantages related to the health of produced plants and efficiency of growth and processing.

Non-limiting embodiments encompassed by the present disclosure include (Stage 1, Stage 2, Stage 3, etc, media are defined elsewhere herein):

I. The following species: *Arundinaria gigantea; Bambusa balcoa; Bambusa vulgaris; Bambusa vulgaris* 'Vitatta'; *Bambusa Oldhamii; Bambusa tulda; endrocalamus brandesii; Dendrocalamus asper; Dendrocalamus hamiltoni; Dendrocalamus giganteus; Dendrocalamus membranaceus; Dendrocalamus strictus; Gigantochloa aspera; Gigantochloa scortechini; Guadua culeata; uadua aculeata* 'Nicaragua'; *Guadua amplexifolia; Guadua angustifolia; Guadua angustofolia* bi-color; *Guadua paniculata; Melocanna bambusoides; eohouzeaua dullooa* (Teinostachyum); *Ochlandra travancorica; Phyllostachys edulis* 'Moso'; *Phyllostachys nigra; Phyllostachys nigra* 'Henon'; *Schizostachyum lumampao;*

II. Stage 1 media: Media b-12-c-v media or b-10-v media;

III. Stage 2 media: CW1-v media; CW2-v media; CW3-v media; CW4-v media; CW5-v media; or CW6-v media for 10-120 day cycles; and IV. Stage 3 media: Br-2-v media; Ech-v media or Amel-v media.

More particularly, the following embodiments can be used (Stage 1, Stage 2, Stage 3, etc, media are defined elsewhere herein):

Starting with a bamboo plant between the ages of 3 months and 3 years, a node from the cane with the lateral shoot just breaking the sheath can be used as the explant. Each nodal section can be cut into 3-5 millimeter sections with the shoot intact. The outer sheaths can be peeled off and discarded and the remaining nodal section piece put into a 10% bleach solution with a final concentration of 0.6% sodium hydrochloride. The explant in bleach solution can be placed onto a Lab Rotators, Adjustable speed, Barnstead/Lab line orbital Shaker (model number KS 260) shaker table for 1 hour at 6-9 revolutions per minute. The explants can then be put into a 1% bleach solution with a final concentration of 0.06% sodium hydrochloride, and be placed back onto the shaker table for 30 minutes. This 1% bleach solution step can then be repeated.

Individual explants can then be placed on a Stage 1 media (15-25 mL) within a tube and the tubes can be placed into a regulated clean growth chamber at a temperature of from 65° F.-70° F. and a full spectrum light level of 200-500 foot candles. The initial Stage 1 media can be b-12c-iv at a pH of 5.7. The explants can then be transferred to fresh b-12c-iv media every 10-120 days (usually every 21 days), with contaminated tubes being discarded. Contaminated tubes can be identified by bacterial discoloration of the agar or by visible surface contamination. These explants can stay on b-12c-iv media for 3-4 10-120 day cycles (usually 21 day cycles). Explants can then be taken off the media after the third cycle if multiplication is occurring. If multiplication is not occurring or not occurring to a significant degree, explants can be left on the media for a fourth cycle.

Live shoots can next be transferred to a Stage 2 media, such as b-9, CW1, CW2, CW3, CW4, CW5, CW6 or b-6 at a pH of 5.7. The cultures can stay on this Stage 2 media until the desired number of shoots is obtained by separation into new tubes and further expansion. Generally, the range of time includes 10-120 day cycles (usually 14-21 day cycles) between which the cultures are assigned to go through another multiplication round in Stage 2 media or transitioned to a Stage 3 media, for example, b-10-iv or b-11-iv at a pH of 5.7 for further multiplication. One-ten shoots per tube can be obtained per multiplication cycle.

Following removal from the multiplication process, the shoots can transferred to small tissue culturing boxes (known as "magenta boxes") for 10-120 days (usually 14-21 days) containing a Stage 3 or Stage 4 media, in this Example, BR-2 at a pH of 5.7 for 10-120 days (usually 14-21 days) or Amel at a pH of 5.7 for 10-120 days (usually 14-21 days).

The following procedures may also be used (Stage 1, Stage 2, Stage 3, etc, media are defined elsewhere herein):

Starting with a bamboo plant between the ages of 3 months and 3 years, a node from the cane with the lateral shoot just breaking the sheath can be used as the explant. Each nodal section can be cut into 3-5 millimeter sections with the shoot intact. Some explants, including explants taken from canes 1 year or older can be pre-rinsed by shaking them in a jar of 70% isopropyl alcohol for 3 seconds followed by rinsing them under running tap water for 1 minute. Other explants are not pre-rinsed.

The outer sheaths can be peeled off and discarded and the remaining nodal section piece put into a 10% bleach solution. The explant in bleach solution can be placed onto a Lab Rotators, Adjustable speed, Barnstead/Lab line orbital Shaker (model number KS 260) shaker table for 1 hour at 6-9 revolutions per minute. For some implants, including those taken from canes 1 year or older, this step can be modified by adding a few drops of Tween 20 to the 10% bleach solution and soaking the explants for 45 minutes rather than 1 hour. The explants can then be put into a 1% bleach solution, and placed back onto the shaker table for 30 minutes. This 1% bleach solution step can then be repeated.

Individual explants can then be placed on a Stage 1 media (15-25 mL) within a tube and the tubes placed into a regulated clean growth chamber at a temperature of from 65° F.-70° F. and a full spectrum light level of 200-500 foot candles. The Stage 1 media can be b-12c-iv at a pH of 5.7. The explants can be transferred to fresh b-12c-iv media every 10-120 days (usually every 21 days), with contaminated tubes being discarded. These explants can stay on b-12c-iv media for 2 10-120 day cycles (usually 21 day cycles). Between cycles, excess sheaths can be removed. At the time of transfer to the third cycle, explants can be transitioned to a Stage 2 media, in this Example, b-12-c supplemented with 7 g/L carageenan rather than the 5.5 g/L provided above. Following the third cycle, explants can be cleaned. The explants can be kept on b-12-c supplemented with 7 g/L carageenan rather than the 5.5 g/L provided above for 10-120 day cycles (usually 21 day cycles) until multiple shoots are observed. Observation of multiple shoots can occur within 3-15 months.

Once the explant exhibits multiple shoots, it can be either maintained on its Stage 2 media or transferred to a Stage 3 media. Non-limiting Stage 3 media include, a b-9 media, a CW1 media, a CW2 media a CW3 media, a CW4 media, a CW5 media, a CW6 media or a b-6 media at a pH of 5.7. The cultures can stay on Stage 2 or Stage 3 media until the desired number of shoots is obtained by separation into new tubes and further expansion. Generally, the range of time includes 10-120 day cycles (usually 21 day cycles) between which the cultures can be assigned to go through another multiplication round or transitioned to a Stage 3 or Stage 4 media, such as a BR-2 media at a pH of 5.7 for 10-120 days (usually 21 days) in "magenta boxes" or a Amel media at a pH of 5.7 for 10-120 days (usually 14-21 days).

In even more particular non-limiting embodiments, the following species can be micropropagated in the following media according to procedures described in the proceeding paragraphs [000137]-[000145], usually as a Stage 2 media, at a pH of 5.5-5.7:

*Arundinaria gigantea*: b-9-v, CW1-v, CW3-v, CW4-v, CW5-v or CW6-v;
*Bambusa balcoa*: b-9-v, CW1-v, CW3-v, CW4-v, CW5-v or CW6-v;
*Bambusa vulgaris*: b-9-v, CW1-v, CW3-v, CW4-v, CW5-v or CW6-v;
*Bambusa vulgaris* 'Vitatta': b-9-v, CW1-v, CW3-v, CW4-v, CW5-v or CW6-v;
*Bambusa Oldhamii*: b-9-v, CW1-v, CW3-v, CW4-v, CW5-v or CW6-v;
*Bambusa tulda*: b-9-v, CW1-v, CW3-v, CW4-v, CW5-v or CW6-v;
*Dendrocalamus brandesii*: b-9-v, CW1-v, CW3-v, CW4-v, CW5-v or CW6-v;
*Dendrocalamus asper*: b-9-v, CW1-v, CW3-v, CW4-v, CW5-v or CW6-v;
*Dendrocalamus hamiltoni*: b-9-v, CW1-v, CW3-v, CW4-v, CW5-v or CW6-v;
*Dendrocalamus giganteus*: b-9-v, CW1-v, CW3-v, CW4-v, CW5-v or CW6-v;
*Dendrocalamus membranaceus*: b-9-v, CW1-v, CW3-v, CW4-v, CW5-v or CW6-v;
*Dendrocalamus strictus*: b-9-v, CW1-v, CW3-v, CW4-v, CW5-v or CW6-v;
*Gigantochloa aspera*: b-9-v, CW1-v, CW3-v, CW4-v, CW5-v or CW6-v;
*Gigantochloa scortechini*: b-9-v, CW1-v, CW3-v, CW4-v, CW5-v or CW6-v;
*Guadua culeata*: b-9-v, CW1-v, CW3-v, CW4-v, CW5-v or CW6-v;
*Guadua aculeata* 'Nicaragua': b-9-v, CW1-v, CW3-v, CW4-v, CW5-v or CW6-v;
*Guadua amplexifolia*: b-9-v, CW1-v, CW3-v, CW4-v, CW5-v or CW6-v;
*Guadua angustifolia*: b-9-v, CW1-v, CW3-v, CW4-v, CW5-v or CW6-v;
*Guadua angustofolia* bi-color: b-9-v, CW1-v, CW3-v, CW4-v, CW5-v or CW6-v;
*Guadua paniculata*: b-9-v, CW1-v, CW3-v, CW4-v, CW5-v or CW6-v;
*Melocanna bambusoides*: b-9-v, CW1-v, CW3-v, CW4-v, CW5-v or CW6-v;
*Neohouzeaua dullooa* (Teinostachyum): b-9-v, CW1-v, CW3-v, CW4-v, CW5-v or CW6-v;
*Ochlandra travancorica*: b-9-v, CW1-v, CW3-v, CW4-v, CW5-v or CW6-v;
*Phyllostachys edulis* 'Moso': b-9-v, CW1-v, CW3-v, CW4-v, CW5-v or CW6-v;
*Phyllostachys nigra*: b-9-v, CW1-v, CW3-v, CW4-v, CW5-v or CW6-v;
*Phyllostachys nigra* 'Henon': b-9-v, CW1-v, CW3-v, CW4-v, CW5-v or CW6-v;
*Schizostachyum lumampao*: b-9-v, CW1-v, CW3-v, CW4-v, CW5-v or CW6-v.

As stated previously, there are many uses for bamboos produced according to the methods disclosed herein. In addition to or complementing those uses described elsewhere, non-limiting examples of uses and products made from bamboos produced according to the media, systems and methods disclosed herein include:

Exemplary Paper Types: Freesheet; Stock; Acid-free; A4; Board; Bond; Book; Bristol; Carbonless; Catalog; Coated; Cover; Dual-Purpose Bond; Duplex; English Finish; Equivalent; Fine; Free Sheet; Grain Long; Grain Short; Groundwood; Kraft; Lightweight; News Print; Publishing; Rag; Recycled; Tag; Uncoated; Virgin; Absorbent; Acid; Album; Albumin; Alkaline; Bank Note; Tissue; Toilet; Towels; Fluff; Card Stock; one-time carbon (OTC); optical character recognition (OCR); Tissue Overlay; and Napkins.

Exemplary Pulp Types: Air-dried; Alpha; Bamboo; Bisulfate; Sulphite; Bleached; Chemical Cellulose (Dissolving); Fluff; Fodder; Free; Fully Bleached; Hard; High Alpha Cellulose; Groundwood; Hot Groundwood; Jute; Knotter; Kraft; Long Fiber; Baled; Rolled; Market; Non-Wood; Board; Pressurized Groundwood; Rag; Recycled; Reinforcement; Secondary; Semi-alkaline; Semi-bleached; Semi-chemical; Short Fiber; Soda; Specialty; Sulfate; Thermochemical; Unbleached; Viscose; and Wood.

Board/Containers: Linerboard; Containerboard; Cardboard; old corrugated containers (OCC); and Paperboard.

Wood: Structural Wood Panels (including Structural Plywood; Oriented Strand Board; Structural Composite Panels); Glued Laminated Timber; Structural Composite Lumber (including Laminated Veneer Lumber; Parallel Strand Lumber; Oriented Strand Lumber); Prefabricated Wood I-Joists; Floor Joints; Railroad Ties; Flooring; and Composites (including Auto; Aero; Musical).

Textiles: Feedstock; Filament Yarn; Knitted Fabric; Knitting; Narrow Width Fabric; Non Woven Fabric; Spun Yarn; Woven Fabric; Viscose Rayon; Batting; Ginned Fiber; and Cloth.

Textile Products: Clothing; Towels; Sheets/Bedding; Pillows; Curtains

Food sources: Shoots; and any direct or bi-product for food consumption by animals and humans.

Consumer Goods: Animal Feed; Carpeting; Light Bulbs; Household Cleaning Products; Chopsticks & Toothpicks; Cleaning Brooms; Bicycles; Wheel Chairs; Fishing rods; Beer; Liquor; Pharmaceuticals; Cosmetics; Soap/Shampoo; Kitchenware; Crafts; Furniture; Nutraceuticals; Paper cups; Paper plates; and Diapers.

Energy & Bioenergy: Charcoal; Insulation; Feedstock; and Biomass.

The following non-limiting examples are provided. In all examples, time on media that supports transition to ex vitro conditions can be in air permeable or air impermeable containers. Described media are utilized in their solid forms provided above unless otherwise noted as liquid.

EXAMPLES

Example 1

*Phyllostachys bissetti*

Starting with a bamboo plant between the ages of 3 months and 3, years, a node from the cane with the lateral shoot just breaking the sheath was used as the explant. Each nodal section was cut into 3-5 millimeter sections with the shoot intact. The outer sheaths were peeled off and discarded and the remaining nodal section piece put into a 10% bleach solution with a final concentration of 0.6% sodium hydrochloride. The explant in bleach solution was placed onto a Lab Rotators, Adjustable speed, Barnstead/Lab line orbital Shaker (model number KS 260) shaker table for 1 hour at 6-9 revolutions per minute. The explants were then put into a 1% bleach solution with a final concentration of 0.06% sodium hydrochloride, and placed back onto the shaker table for 30 minutes. This 1% bleach solution step was then repeated.

Individual explants were then placed on a Stage 1 media (15-25 mL) within a tube and the tubes were placed into a regulated clean growth chamber at a temperature of from 65° F.-70° F. and a full spectrum light level of 200-500 foot candles. The initial Stage 1 media in this Example was b-12c-iv at a pH of 5.7. The explants were transferred to fresh b-12c-iv media every 10-120 days (usually every 21 days), with contaminated tubes being discarded. Contaminated tubes were identified by bacterial discoloration of the agar or by visible surface contamination. These explants stayed on b-12c-iv media for 3-4 10-120 day cycles (usually 21 day cycles). Explants were taken off the media after the third cycle if multiplication was occurring. If multiplication was not occurring or not occurring to a significant degree, explants were left on the media for a fourth cycle.

Live shoots were next transferred to a Stage 2 media, in this Example, b-9-iv at a pH of 5.7. The cultures stayed on b-9-iv media until the desired number of shoots was obtained by separation into new tubes and further expansion. Generally, the range of time included 10-120 day cycles (usually 14-21 day cycles) between which the cultures were assigned to go through another multiplication round in Stage 2 media or transitioned to a Stage 3 media, in this Example, b-10-iv at a pH of 5.7 for further multiplication. One-ten shoots per tube were obtained per multiplication cycle.

Following removal from the multiplication process, the shoots were transferred to small tissue culturing boxes (known as "magenta boxes") for 10-120 days (usually 14-21 days) containing a Stage 3 or Stage 4 media, in this Example. BR-2-iv at a pH of 5.7 for 10-120 days (usually 14-21 days).

Example 2

*Fargesia denudate*

In the example of *Fargeria denudata*, the explants were chosen and disinfected as in Example 1.

The explants were then transferred into jars containing a Stage 1 media, in this Example, b-12c-iv (liquid; 30-40 mL) as described in Example 1 but for the use of jars. Explants were taken off the media after the third cycle if multiplication was occurring. If multiplication was not occurring or not occurring to a significant degree, explants were left on the media for a fourth cycle. Contaminated tubes were discarded.

The cultures were then transferred onto a Stage 2 media, in this Example, b-11-iv (liquid) in jars on a rotating shelf that provides 6-9 revolutions per minute. The cultures remained on b-11-iv media at a pH of 5.7 for 10-120 day cycles (usually 14 day cycles) until the desired number of shoots was obtained by separation into new jars and further expansion. One-fifteen shoots per jar were obtained per multiplication cycle. The shoots were then placed in a Stage 3 media, in this Example, Ech-iv at a pH of 6 for 10-120 days (usually 14-21 days).

Example 3

*Pleioblastus fortunei*

In the example of *Pleioblastus fortunei*, the explants were chosen and disinfected as in Example 1. The explants were then transferred into tubes containing a Stage 1 media, in this Example, b-12c-iv also as described in Example 1. Shoots were then transferred to a Stage 2 media, in this Example, b-9-iv in magenta boxes (40-50 mL). They remained on b-9-iv media for 10-120 day cycles (usually 14 day cycles) until the desired number of shoots was obtained by separation into new boxes and further expansion. One-twenty shoots per box were obtained per multiplication cycle. The shoots were then placed on a Stage 3 media, in this Example, BR-2-iv for 10-120 days (usually 14-21 days).

Example 4

*Sasa Veitchii*

In the example of *Sasa Veitchii*, the explants were chosen and disinfected as in Example 1.

The explants were then transferred into tubes containing a Stage 1 media, in this Example, b-12c-iv also as described in Example 1. Shoots were then transferred into a Stage 2 media, in this Example, b-1-iv at a pH of 5.5 for 10-120 day cycles (usually 21 day cycles) until the desired number of shoots was obtained by separation into new tubes and further expansion One-ten shoots per tube were obtained per multiplication cycle. The shoots were then placed in a Stage 3 media, in this Example, Br-2-iv at a pH of 5.7 for 14-21 days.

Example 5

*Pleioblastus viridistriatus* and *Thamnocalamus crassinodus*

In the example of *Pleioblastus viridistriatus* and *Thamnocalamus crassinodus*, the explants were chosen and disinfected as in Example 1. The explants were then transferred into tubes containing a Stage 1 media, in this Example, b-12c-iv also as described in Example 1. Shoots were then transferred into a Stage 2 media, in this Example, b-4-iv at a pH of 5.5 for 10-120 day cycles (usually 21 day cycles) until the desired number of shoots was obtained by separation into new tubes and further expansion. One-ten shoots per tube were obtained per multiplication cycle. The shoots were then placed in a Stage 3 media, in this Example, Br-2-iv at a pH of 5.7 for 10-120 days (usually 14-21 days).

Example 6

*Chusquea Culeo* "Cana Prieta"

In the example of *Chusquea Culeo* "Cana Prieta", the explants were chosen and disinfected as in Example 1. The explants were then transferred into tubes containing a Stage 1 media, in this Example, b-12c-iv media also as described in Example 1. Shoots were then transferred into a Stage 2 media, in this Example, b-9-iv at a pH of 5.5 for 10-120 day cycles (usually 21 day cycles) until the desired number of shoots was obtained by separation into new tubes and further expansion. One-ten shoots per tube were obtained per multiplication cycle. The shoots were then placed in a Stage 3 media, in this Example, Amel-iv at a pH of 5.7 for 10-120 days (usually 14-21 days).

Example 7

Bambusa Old Hamii

In the example of Bambusa Old amii, the explants were chosen and disinfected as in Example 1. The explants were then transferred into boxes containing a Stage 1 media, in this Example, b-10-iv (40-50 mL) also as described in Example 1 but for the change to boxes. Shoots were maintained on b-10-iv media for 10-120 day cycles (usually 21 day cycles) until the desired number of shoots was obtained by separation into new boxes and further expansion. One-twenty shoots per box were obtained per multiplication cycle. The shoots were then placed in a Stage 2 media, in this Example, Amel-iv at a pH of 5.7 for 10-120 days (usually 14-21 days).

Example 8

*Phyllostachys Edulis* "Moso", *Phyllostachys Atrovaginata* & *Dendrocalamus Asper*

In the example of *Phyllostachys Edulis* "Moso", *Phyllostachys Atrovaginata* & *Dendrocalamus Asper*, the explants were chosen and disinfected as in Example 1. The explants were then transferred into tubes containing a Stage 1 media, in this Example, b-12c-iv also as described in Example 1. Shoots were then transferred into a Stage 2 media, in this Example, b-9-iv at a pH of 5.5 for 10-120 day cycles (usually 21 day cycles) until the desired number of shoots was obtained by separation into new tubes and further expansion. A B-6 media at a pH of 5.5 can also be used. One-ten shoots per tube were obtained per multiplication cycle. The shoots were then placed in a Stage 3 media, in this Example, Amel-iv at a pH of 5.7 for 10-120 days (usually 14-21 days).

Example 9

*Guadua Angustifolia*

In the example of *Guadua Angustofolia*, the explants were chosen and disinfected as in Example 1. The explants were then transferred into tubes containing a Stage 1 media, in this Example, b-12c-iv also as described in Example 1. Shoots were then transferred into a Stage 2 media, in this Example, b-10-iv at a pH of 5.5 for 10-120 day cycles (usually 21 day cycles) until the desired number of shoots was obtained by separation into new tubes and further expansion. One-ten shoots per tube were obtained per multiplication cycle. The shoots were then placed in a Stage 3 media, in this Example, Amel-iv at a pH of 5.7 for 10-120 days (usually 14-21 days).

Example 10

*Phyllostachys bissetti*—Alternate Procedure

Starting with a bamboo plant between the ages of 3 months and 3 years, a node from the cane with the lateral shoot just breaking the sheath was used as the explant. Each nodal section was cut into 3-5 millimeter sections with the shoot intact. Some explants, including explants taken from canes 1 year or older were pre-rinsed by shaking them in a jar of 70% isopropyl alcohol for 3 seconds followed by rinsing them under running tap water for 1 minute. Other explants were not pre-rinsed.

The outer sheaths were peeled off and discarded and the remaining nodal section piece put into a 10% bleach solution. The explant in bleach solution was placed onto a Lab Rotators, Adjustable speed, Barnstead/Lab line orbital Shaker (model number KS 260) shaker table for 1 hour at 6-9 revolutions per minute. For some implants, including those taken from canes 1 year or older, this step was modified by adding a few drops of Tween 20 to the 10% bleach solution and soaking the explants for 45 minutes rather than 1 hour. The explants were then put into a 1% bleach solution, and placed back onto the shaker table for 30 minutes. This 1% bleach solution step was then repeated.

Individual explants were then placed on a Stage 1 media (15-25 mL) within a tube and the tubes were placed into a regulated clean growth chamber at a temperature of from 65° F.-70° F. and a full spectrum light level of 200-500 foot candles. In this Example, the Stage 1 media was b-12c-iv at a pH of 5.7. The explants were transferred to fresh b-12c-iv media every 10-120 days (usually every 21 days), with contaminated tubes being discarded. These explants stayed on b-12c-iv media for 2 10-120 day cycles (usually 21 day cycles). Between cycles, excess sheaths were removed. At the time of transfer to the third cycle, explants were transitioned to a Stage 2 media, in this Example, b-12-c supplemented with 7 g/L carageenan rather than the 5.5 g/L provided above. Following the third cycle, explants were cleaned. The explants were kept on b-12-c supplemented with 7 g/L carageenan for 10-120 day cycles (usually 21 day cycles) until multiple shoots were observed. Observation of multiple shoots occurred within 3-15 months.

Once the explant exhibited multiple shoots, it was either maintained on its Stage 2 media or transferred to a Stage 3 media, in this Example, when used b-9-iv at a pH of 5.7. Alternatively to using one of the B-9 media, a CW1 media at a pH of 5.7 can also be used. The cultures stayed on Stage 2 or Stage 3 media until the desired number of shoots was obtained by separation into new tubes and further expansion. Generally, the range of time included 10-120 day cycles (usually 21 day cycles) between which the cultures were assigned to go through another multiplication round or were transitioned to a Stage 3 or Stage 4 media, in this Example, BR-2-iv at a pH of 5.7 for 10-120 days (usually 21 days) in "magenta boxes".

Example 11

*Fargesia denudata*—Alternate Procedure

In the example of *Fargeria denudata*, the explants were chosen and disinfected as in Example 10. The explants were then transferred into jars containing a Stage 1 media, in this Example, b-12c-iv (liquid; 30-40 mL) as described in Example 10 but for the use of jars. These explants stayed on b-12c-iv media for 2 10-120 day cycles (usually 21 day cycles). Between cycles, excess sheaths were removed. At the time of transfer to the third cycle, explants were transitioned to a Stage 2 media, in this Example, b-12-c supplemented with 7 g/L carageenan rather than the 5.5 g/L provided above. Following the third cycle, explants were cleaned. The explants were kept on b-12-c supplemented with 7 g/L carageenan for 10-120 day cycles (usually 21 day cycles) until multiple shoots were observed. Observation of multiple shoots occurred within 3-15 months.

Once the explant exhibited multiple shoots, it was either maintained on its Stage 2 media or transferred to a Stage 3 media, in this Example, b-11-iv (liquid) at a pH of 5.7 in jars on a rotating shelf that provides 6-9 revolutions per minute. The cultures remained on Stage 2 or Stage 3 media for 10-120 day cycles (usually 14 day cycles) until the desired number of shoots was obtained by separation into new jars and further expansion. One-fifteen shoots per jar were obtained per multiplication cycle. The shoots were then placed in a Stage 3 or Stage 4 media, in this Example, Ech-iv at a pH of 6 for 10-120 days (usually 21 days).

Example 12

*Pleioblastus fortunei*—Alternate Procedure

In the example of *Pleioblastus fortunei*, the explants were chosen and disinfected as in Example 10. The explants were then transferred into tubes containing a Stage 1 media in this Example, b-12c-iv also as described in Example 10. These explants stayed on b-12c-iv media for 2 10-120 day cycles (usually 21 day cycles). Between cycles, excess sheaths were removed. At the time of transfer to the third cycle, explants were transitioned to a Stage 2 media, in this Example, b-12-c supplemented with 7 g/L carageenan rather than the 5.5 g/L provided above. Following the third cycle, explants were cleaned. The explants were kept on b-12-c supplemented with 7 g/L carageenan for 10-120 day cycles (usually 21 day cycles) until multiple shoots were observed. Observation of multiple shoots occurred within 3-15 months.

Once the explant exhibited multiple shoots, it was either maintained on its Stage 2 media or transferred to a Stage 3 media, in this Example b-9-iv in magenta boxes (40-50 mL). (CW1 media can also be used). They remained on b-9-iv media for 10-120 day cycles (usually 14 day cycles) until the desired number of shoots was obtained by separation into new boxes and further expansion. One-twenty shoots per box were obtained per multiplication cycle. The shoots were then placed in a Stage 3 or Stage 4 media, in this Example, BR-2-iv for 10-120 days (usually 14-21 days).

Example 13

*Sasa Veitchii*—Alternate Procedure

In the example of *Sasa Veitchii*, the explants were chosen and disinfected as in Example 10.

The explants were then transferred into tubes containing a Stage 1 media, in this Example, b-12c-iv also as described in Example 10. These explants stayed on b-12c-iv media for 2 10-120 day cycles (usually 21 day cycles). Between cycles, excess sheaths were removed. At the time of transfer to the third cycle, explants were transitioned to a Stage 2 media, in this Example, b-12-c supplemented with 7 g/L carageenan rather than the 5.5 g/L provided above. Following the third cycle, explants were cleaned. The explants were kept on b-12-c supplemented with 7 g/L carageenan for 10-120 day cycles (usually 21 day cycles) until multiple shoots were observed. Observation of multiple shoots occurred within 3-15 months.

Once the explant exhibited multiple shoots, it was either maintained on its Stage 2 media or transferred to a Stage 3 media, in this Example b-1-iv at a pH of 5.5 for 10-120 day cycles (usually 21 day cycles) until the desired number of shoots was obtained by separation into new tubes and further expansion One-ten shoots per tube were obtained per multiplication cycle. The shoots were then placed in a Stage 3 or Stage 4 media, in this Example, Br-2-iv at a pH of 5.7 for 10-120 days (usually 14-21 days).

Example 14

*Pleioblastus viridistriatus* and *Thamnocalamus crassinodus*—Alternate Procedure In the example of *Pleioblastus viridistriatus* and *Thamnocalamus crassinodus*, the explants were chosen and disinfected as in Example 10. The explants were then transferred into tubes containing a Stage 1 media, in this Example, b-12c-iv also as described in Example 10. These explants stayed on b-12c-iv media for 2 10-120 day cycles (usually 21 day cycles). Between cycles, excess sheaths were removed. At the time of transfer to the third cycle, explants were transitioned to a Stage 2 media, in this Example, b-12-c supplemented with 7 g/L carageenan rather than the 5.5 g/L provided above. Following the third cycle, explants were cleaned. The explants were kept on b-12-c supplemented with 7 g/L carageenan for 10-120 day cycles (usually 21 day cycles) until multiple shoots were observed. Observation of multiple shoots occurred within 3-15 months.

Once the explant exhibited multiple shoots, it was either maintained on its Stage 2 media or transferred to a Stage 3 media, in this Example b-4-iv at a pH of 5.5 for 10-120 day cycles (usually 21 day cycles) until the desired number of shoots was obtained by separation into new tubes and further expansion. One-ten shoots per tube were obtained per multiplication cycle. The shoots were then placed in a Stage 3 or Stage 4 media, in this Example, Br-2-iv at a pH of 5.7 for 10-120 days (usually 14-21 days).

Example 15

*Chusquea Culeo* "Cana Prieta"—Alternate Procedure

In the example of *Chusquea Culeo* "Cana Prieta", the explants were chosen and disinfected as in Example 10. The explants were then transferred into tubes containing a Stage 1 media, in this Example, b-12c-iv also as described in Example 10. These explants stayed on b-12c-iv media for 2 10-120 day cycles (usually 21 day cycles). Between cycles, excess sheaths were removed. At the time of transfer to the third cycle, explants were transitioned to a Stage 2 media, in this Example, b-12-c supplemented with 7 g/L carageenan rather than the 5.5 g/L provided above. Following the third cycle, explants were cleaned. The explants were kept on b-12-c supplemented with 7 g/L carageenan for 10-120 day cycles (usually 21 day cycles) until multiple shoots were observed. Observation of multiple shoots occurred within 3-15 months.

Once the explant exhibited multiple shoots, it was either maintained on its Stage 2 media or transferred to a Stage 3 media, in this Example b-9-iv at a pH of 5.5 for 10-120 day cycles (usually 21 days) until the desired number of shoots was obtained by separation into new tubes and further expansion. A B-6 media at a pH of 5.5 can also be used. One-ten shoots per tube were obtained per multiplication cycle. The shoots were then placed in a Stage 3 or Stage 4 media, in this Example, Amel-iv media at a pH of 5.7 for 10-120 days (usually 14-21 days).

Example 16

Bambusa Old Hami—Alternate Procedure

In the example of Bambusa Old amii, the explants were chosen and disinfected as in Example 10. The explants were then transferred into boxes containing a Stage 1 media, in this Example, b-10-iv (40-50 mL) also as described in Example 10 but for the change to boxes. These explants stayed on b-10-iv media for 2 10-120 day cycles (usually 21 day cycles). Between cycles, excess sheaths were removed. At the time of transfer to the third cycle, explants were transitioned to a Stage 2 media, in this Example, b-10-c supplemented with 7 g/L carageenan rather than the 5.5 g/L provided above. Following the third cycle, explants were cleaned. The explants were kept on b-10-c supplemented with 7 g/L carageenan for 10-120 day cycles (usually 21 day cycles) until multiple shoots were observed. Observation of multiple shoots occurred within 3-15 months. Cultures were maintained on Stage 2 media until the desired number of shoots was obtained. One-twenty shoots per box were obtained per multiplication cycle. The shoots were then placed in a Stage 3 media, in this Example, Amel-iv at a pH of 5.7 for 10-120 days (usually 14-21 days).

Example 17

*Phyllostachys Moso, Phyllostachys Atrovaginata & Dendrocalamus Asper*—Alternate Procedure In the example of *Phyllostachys Moso, Phyllostachys Atrovaginata* and *Dendrocalamus Asper*, the explants were chosen and disinfected as in Example 10. The explants were then transferred into tubes containing a Stage 1 media, in this Example, b-12c-iv also as described in Example 10. These explants stayed on b-12c-iv media for 2 10-120 day cycles (usually 21 day cycles). Between cycles, excess sheaths were removed. At the time of transfer to the third cycle, explants were transitioned to a Stage 2 media, in this Example, b-12-c supplemented with 7 g/L carageenan rather than the 5.5 g/L provided above. Following the third cycle, explants were cleaned. The explants were kept on b-12-c supplemented with 7 g/L carageenan for 10-120 day cycles (usually 21 day cycles) until multiple shoots were observed. Observation of multiple shoots occurred within 3-15 months.

Once the explant exhibited multiple shoots, it was either maintained on its Stage 2 media or transferred to a Stage 3 media, in this Example b-9-iv at a pH of 5.5 for 10-120 day cycles (usually 21 day cycles) until the desired number of shoots was obtained by separation into new tubes and further expansion. A B-6 media at a pH of 5.5 can also be used. One-ten shoots per tube were obtained per multiplication cycle. The shoots were then placed in a Stage 3 or Stage 4 media, in this Example, Amel-iv at a pH of 5.7 for 10-120 days (usually 14-21 days).

Example 18

*Guadua Angustifolia*—Alternate Procedure

In the example of *Guadua Angustofolia*, the explants were chosen and disinfected as in Example 10. The explants were then transferred into tubes containing a Stage 1 media, in this Example, b-12c-iv also as described in Example 10. These explants stayed on b-12c-iv media for 2 10-120 day cycles (usually 21 day cycles). Between cycles, excess sheaths were removed. At the time of transfer to the third cycle, explants were transitioned to a Stage 2 media, in this Example, b-12-c supplemented with 7 g/L carageenan rather than the 5.5 g/L provided above. Following the third cycle, explants were cleaned. The explants were kept on b-12-c supplemented with 7 g/L carageenan for 10-120 day cycles (usually 21 day cycles) until multiple shoots were observed. Observation of multiple shoots occurred within 3-15 months.

Once the explant exhibited multiple shoots, it was either maintained on its Stage 2 media or transferred to a Stage 3 media, in this Example b-10-iv at a pH of 5.5 for 10-120 day cycles (usually 21 day cycles) until the desired number of shoots was obtained by separation into new tubes and further expansion. One-ten shoots per tube were obtained per multi-plication cycle. The shoots were then placed in a Stage 3 or Stage 4 media, in this Example, Amel-iv at a pH of 5.7 for 10-120 days (usually 14-21 days).

As will be understood by one of ordinary skill from the provided examples, the tissue culturing method for individual species includes slight variations in media, timing and growth conditions. These variations for individual species require optimization based on factors including location, desired outcome, starting material, etc.

For each of the species provided in the examples listed above, in particular embodiments, each can be initiated and/or multiplied in b-9-i media, b-9-ii media, b-9-iii media, b-9-iv media, b-9-v media, CW2-i media, CW2-ii media, CW2-iii media, CW2-iv media, CW2-v media, b-10-i media, b-10-ii media, b-10-iii media, b-10-iv media, b-10-v media, b-11-i media, b-11-ii media, b-11-iii media, b-11-iv media, b-11-v media, b-12c-i media, b-12c-ii media, b-12c-iii media, b-12c-iv media, b-12c-v media, b-1-i media, b-1-ii media, b-1-iii media, b-1-iv media, b-1-v media, b-4-i media, b-4-ii media, b-4-iii media, b-4-iv media, b-4-v media, b-6-i media, b-6-ii media, b-6-iii media, b-6-iv media, b-6-v media, CW1-i media, CW1-ii media, CW1-iii media, CW1-iv media, CW1-v media, CW3-i media, CW3-ii media, CW3-iii media, CW3-iv media, CW3-v media, CW4-i media, CW4-ii media, CW4-iii media, CW4-iv media, CW4-v media, CW5-i media, CW5-ii media, CW5-iii media, CW5-iv media, CW5-v media, CW6-i media, CW6-ii media, CW6-iii media, CW6-iv media and/or CW6-v media.

As used herein "in" and "on" are interchangeable in the context of placing explants, shoots or plantlets within a tube, jar, box or jug containing a media.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for micropropagating bamboo, comprising: initiating a shoot in vitro from a bamboo explant of a first media, and multiplying the shoot initiated from the explant in vitro on a second media, wherein the bamboo explant comprises plant tissue from a lateral shoot of a bamboo plant, and wherein the first media comprises meta-topolin (mT) and thidiazuron (TDZ), and the second media comprises meta-topolin and optionally thidiazuron (TDZ).

2. The method of claim 1, wherein the plant tissue comprises a nodal section of the lateral shoot.

3. The method of claim 1, wherein the bamboo explant is from a bamboo plant ranging in age from about 3 months to about 3 years.

4. The method of claim 1, wherein at least three in vitro shoots are obtained from the explant following multiplication.

5. The method of claim 4, wherein the method further comprises separating and individually transferring the at least three in vitro shoots to fresh first media or fresh second media.

6. The method of claim 1, wherein the method comprises two or more cycles of growing the explant on a fresh first media prior to multiplying the shoot initiated from the explant in vitro on the second media, and/or two or more cycles of growing the initiated shoot on a fresh second media.

7. The method of claim 1, wherein the bamboo is *Phyllostachys edulis*.

8. The method of claim 1, wherein the bamboo is *Phyllostachys bissetti; Fargesia denudata; Pleioblastus fortunei; Sasa Veitchii; Pleioblastus viridistriatus; Thamnocalamus crassinodus; Chusquea Culeo* "Cana Prieta"; *Bambusa Old Hamii; Phyllostachys Atrovaginata; Dendrocalamus Asper; Guadua Angustifolia, Arundinaria gigante; Arundinaria gigantea* 'Macon'; *Bambusa balcooa; Bambusa bambos; Bambusa lako; Bambusa stenostachya; Bambusa tulda; Bambusa vulgaris; Bambusa vulgaris* 'Vittata'; *Chusquea andina; Chusquea gigantea; Dendrocalamus brandisii; Dendrocalamus giganteus; Dendrocalamus hamiltonii; Dendrocalamus latiflorus; Dendrocalamus membranaceus; Dendrocalamus strictus; Fargesia murieliae; Fargesia nitida; Fargesia nitida* 'Jiuzhaigou'; *Fargesia robusta; Fargesia* sp. 'Scrabrida'; *Gigantochloa apus; Gigantochloa pseudoarundinacea; Guadua amplexifolia; Guadua chacoensis; Ochlandra stridula; Ochlandra travancorica; Phyllostachys bambusoides; Phyllostachys dulcis; Phyllostachys nigra; Phyllostachys nigra* 'Bory'; *Phyllostachys nigra* 'Henon'; *Phyllostachys nuda; Phyllostachys rubromarginata; Phyllostachys vivax; Pseudosasa japonica*; or *Semiarundinaria fastuosa*.

9. The method of claim 1, wherein the first media and/or the second media further comprises benzylaminopurine (BAP), and/or β-naphthoxyacetic acid (NAA), and/or 6-γ-γ-(dimethylallylamino)-purine (2-ip), and/or indole butyric acid (IBA).

10. A method for micropropagating bamboo, comprising: initiating a shoot in vitro from a bamboo explant comprising plant tissue from a lateral shoot of a bamboo plant, on a first media comprising meta-topolin and thidiazuron (TDZ); and multiplying the in vitro shoot on a second media comprising meta-topolin (mT) and benzylaminopurine (BAP); and transferring the multiplied in vitro shoots to a third media that supports transition to ex vitro conditions.

11. The method of claim 10, wherein the plant tissue comprises a nodal section of the lateral shoot.

12. The method of claim 10, wherein the bamboo explant is from a bamboo plant ranging in age from about 3 months to about 3 years.

13. The method of claim 10, wherein at least three in vitro shoots are obtained from the explant following multiplication.

14. The method of claim 13, wherein the method further comprises separating and individually transferring the at least three in vitro shoots to fresh first media or fresh second media.

15. The method of claim 10, wherein the method comprises two or more cycles of growing the explant on a fresh first media prior to multiplying the shoot initiated from the explant in vitro on the second media, and/or two or more cycles of growing the initiated shoot on a fresh second media.

16. The method of claim 10, wherein the bamboo is *Phyllostachys edulis*.

17. The method of claim 10, wherein the bamboo is *Phyllostachys bissetti; Fargesia denudata; Pleioblastus fortunei; Sasa Veitchii; Pleioblastus viridistriatus; Thamnocalamus crassinodus; Chusquea Culeo* "Cana Prieta"; *Bambusa Old Hamii; Phyllostachys Atrovaginata; Dendrocalamus Asper; Guadua Angustifolia; Arundinaria gigante; Arundinaria gigantea* 'Macon'; *Bambusa balcooa; Bambusa bambos;*

*Bambusa lako; Bambusa stenostachya; Bambusa tulda; Bambusa vulgaris; Bambusa vulgaris* 'Vittata'; *Chusquea andina; Chusquea gigantea; Dendrocalamus brandisii; Dendrocalamus giganteus; Dendrocalamus hamiltonii; Dendrocalamus latiflorus; Dendrocalamus membranaceus; Dendrocalamus strictus; Fargesia murieliae; Fargesia nitida; Fargesia nitida* 'Jiuzhaigou'; *Fargesia robusta; Fargesia* sp. 'Scrabrida'; *Gigantochloa apus; Gigantochloa pseudoarundinacea; Guadua amplexifolia; Guadua chacoensis; Ochlandra stridula; Ochlandra travancorica; Phyllostachys bambusoides; Phyllostachys dulcis; Phyllostachys nigra; Phyllostachys nigra* 'Bory'; *Phyllostachys nigra* 'Henon'; *Phyllostachys nuda; Phyllostachys rubromarginata; Phyllostachys vivax; Pseudosasa japonica*; or *Semiarundinaria fastuosa*.

18. The method of claim 10, wherein the first media and/or the second media comprises β-napthoxyacetic acid (NAA), and/or 6-y-y (dimethylallylamino)-purine (2ip), and/or indole butyric acid (IBA), and/or wherein the first medium comprises BAP.

* * * * *